United States Patent
Mathurine et al.

(10) Patent No.: US 12,207,056 B2
(45) Date of Patent: Jan. 21, 2025

(54) SYSTEM FOR CONFIGURING A HEARING DEVICE

(71) Applicant: NUHEARA IP PTY LTD, Northbridge (AU)

(72) Inventors: Clint Mathurine, Bayswater (AU); Andrew Victor Cammell, Beeliar (AU); Gregory Paul Breen, Nedlands (AU); Peng Jiang, Morwell (AU); David Ronald Ward, Mosman Park (AU); Alan Davis, Riverton (AU)

(73) Assignee: NUHEARA IP PTY LTD, Northbridge (AU)

( * ) Notice: Subject to any disclaimer, the term of this patent is extended or adjusted under 35 U.S.C. 154(b) by 0 days.

(21) Appl. No.: 18/396,024

(22) Filed: Dec. 26, 2023

(65) Prior Publication Data
US 2024/0129680 A1 Apr. 18, 2024

Related U.S. Application Data

(63) Continuation of application No. 17/884,130, filed on Aug. 9, 2022, now Pat. No. 11,889,273, which is a
(Continued)

(30) Foreign Application Priority Data

May 19, 2017 (AU) .................. 2017901904

(51) Int. Cl.
*H04R 25/00* (2006.01)
*A61B 5/00* (2006.01)
*A61B 5/12* (2006.01)

(52) U.S. Cl.
CPC ............ *H04R 25/70* (2013.01); *A61B 5/123* (2013.01); *A61B 5/4023* (2013.01); *A61B 5/746* (2013.01);
(Continued)

(58) Field of Classification Search
CPC .................. H04R 2225/43; H04R 25/505; H04R 25/558; H04R 25/70; H04R 25/75
(Continued)

(56) References Cited

U.S. PATENT DOCUMENTS 8,144,909 B2   3/2012   Hillbratt et al.
9,119,574 B2   9/2015   Bromwich et al.
(Continued)

OTHER PUBLICATIONS

U.S. Appl. No. 17/884,130, filed Aug. 9, 2022, Mathurine et al.
(Continued)

*Primary Examiner* — Phylesha Dabney
(74) *Attorney, Agent, or Firm* — Crowell & Moring LLP; John C. Freeman

(57) ABSTRACT

A hearing assistance system is disclosed that comprises a hearing assistance device configured to reproduce sounds and to assist a person to hear the sounds, the hearing assistance device including a left hearing assistance device and a right hearing assistance device, and a computing device in communication with the hearing assistance device. The computing device interacts with the hearing assistance device to implement a fitting mode wherein the hearing assistance device is caused to generate fitting sounds usable to evaluate whether the left and right hearing devices are properly fitted into respective left and right ears of the person. The computing device produces a communication indicative of whether the left and right hearing assistance devices are properly fitted into respective left and right ears of the person.

18 Claims, 14 Drawing Sheets

Related U.S. Application Data continuation of application No. 16/612,633, filed as application No. PCT/AU2018/050480 on May 18, 2018, now Pat. No. 11,445,313.

(52) U.S. Cl.
CPC ......... *H04R 25/505* (2013.01); *H04R 25/558* (2013.01); *A61B 2560/0242* (2013.01); *H04R 2225/43* (2013.01)

(58) Field of Classification Search
USPC .......................................... 381/314
See application file for complete search history.

(56) References Cited

U.S. PATENT DOCUMENTS

| | | | |
|---|---|---|---|
| 9,525,951 | B2 | 12/2016 | Park |
| 9,930,454 | B2 * | 3/2018 | van't Hof ............. H04R 25/30 |
| 10,149,067 | B2 | 12/2018 | Kim et al. |
| 11,445,313 | B2 | 9/2022 | Mathurine et al. |
| 2010/0041940 | A1 | 2/2010 | Hillbratt et al. |
| 2012/0215056 | A1 | 8/2012 | Hillbratt et al. |
| 2013/0060159 | A1 | 3/2013 | Bromwich et al. |
| 2013/0337786 | A1 | 12/2013 | Park |
| 2015/0271607 | A1 | 9/2015 | Sabin |
| 2015/0271608 | A1 | 9/2015 | Sabin |
| 2016/0183009 | A1 | 6/2016 | Kim et al. |
| 2017/0289714 | A1 | 10/2017 | Hillbratt et al. |

OTHER PUBLICATIONS

Search Report (9 pages) dated Apr. 19, 2018 from Australian priority Application 2017901904.
Search Report (4 pages) dated Jul. 25, 2018 from corresponding PCT Application PCT/AU2018/050480.
Written Opinion (6 pages) dated Jul. 25, 2018 from corresponding PCT Application PCT/AU2018/050480.
Notification and International Preliminary Report on Patentability (98 pages) dated May 20, 2019 from corresponding PCT Application PCT/AU2018/050480.

* cited by examiner

SYSTEM FOR CONFIGURING A HEARING DEVICE

This application is a continuation application of U.S. patent application Ser. No. 17/884,130, filed on Aug. 9, 2022 (pending), which is a continuation application of U.S. patent application Ser. No. 16/612,633, filed on Nov. 11, 2019 (now U.S. Pat. No. 11,445,313), which is a National Stage application of International Application No. PCT/AU2018/050480, filed May 18, 2018, wherein the above-mentioned International Application claims under 35 U.S.C. § 119(a) the benefit of the filing date of May 19, 2017 of Australian Patent Application No. 2017901904, the entire contents of each of which are incorporated herein by reference.

FIELD OF THE INVENTION

The present invention relates to a system for configuring a hearing device.

BACKGROUND OF THE INVENTION

When a person suspects that he/she has difficulty hearing, the person may seek advice from a hearing health professional such as an audiologist, pharmacist or other health care professional. The degree of hearing loss experienced can be diagnosed by completing a hearing test, which generally produces an audiogram showing hearing thresholds (dB) at several test frequencies (Hz) separately for left and right ears. The audiogram is a direct representation of the hearing capabilities of a person and can be used to form the basis of a prescription and configuration of a hearing device such as a hearing aid or other hearing assistance instrument. A printed or electronically stored copy of the audiogram is typically given to the person by the hearing health professional.

However, an audiogram is difficult for a lay person to understand and interpret, which necessitates the person using a hearing health professional to appropriately configure the hearing assistance device.

It is also known that people with diagnosed hearing loss often choose not to accept a hearing device when an audiogram is produced despite being offered one and despite receiving advice that it may improve their hearing capabilities.

SUMMARY OF THE INVENTION

Disclosed is a system for configuring a hearing device, the system comprising:
  an audiogram processing component arranged to process image data indicative of an image of an audiogram associated with a person so as to produce audiogram data indicative of the audiogram; and
  a hearing device configuration component arranged to produce hearing device configuration data based on the audiogram data, the configuration data indicative of configuration settings for a hearing device that will cause the hearing device to assist the hearing of the person;
  wherein the hearing device configuration component is arranged to obtain information indicative of the capabilities of the hearing device and to produce configuration data using the information indicative of the device capabilities of the hearing device.

In an embodiment, the system comprises a camera arranged to capture image data indicative of an audiogram.

In an embodiment, the system is arranged to enable a user to align an audiogram with an image capture frame, for example using gestures, in order to capture the image data indicative of the audiogram.

In an embodiment, the system is arranged to receive image data indicative of an audiogram through a communications link, for example using USB, Bluetooth or Wi-Fi protocols.

In an embodiment, the system is arranged to obtain air conduction measurements from the audiogram and to include data indicative of the air conduction measurements in the audiogram data.

In an embodiment, the system is arranged to obtain bone conduction measurements from the audiogram and to include data indicative of the bone conduction measurements in the audiogram data.

In an embodiment, the audiogram processing component is arranged to process image data indicative of an image of an audiogram so as to produce audiogram data indicative of the audiogram using a template matching process, for example by localising common audiogram symbols and structure.

In an embodiment, the audiogram processing component is arranged to process image data indicative of an image of an audiogram so as to produce audiogram data indicative of the audiogram using support vector machines.

In an embodiment, the audiogram processing component is arranged to process image data indicative of an image of an audiogram so as to produce audiogram data indicative of the audiogram using at least one neural network.

In an embodiment, the hearing device configuration component is arranged to use formulae NAL-R, NAL-NL1 or NAL-NL2 to produce the hearing device configuration data from the audiogram data.

In an embodiment, the hearing device configuration component is arranged to use configuration information indicative of the age and sex of a person, whether the person is an experienced hearing device user, and/or the primary language of the person to produce the hearing device configuration data from the audiogram data.

In an embodiment, the hearing device configuration component is arranged to produce configuration data in consideration of the device capabilities of the hearing device.

In an embodiment, the system is arranged to query the hearing device for the device capabilities.

In an embodiment, the system is arranged to enable an operator to manually enter the device capabilities.

In an embodiment, the system is arranged to retrieve device capabilities associated with the hearing device from a storage device.

The system may include the storage device. Alternatively, the storage device may be in networked communication with the system such that the storage device is accessible by the system through a network.

In an embodiment, the system is arranged to query the hearing device in order to obtain identification information indicative of the type of hearing device, and to use the identification information to retrieve the device capabilities associated with the hearing device from the storage device.

In an embodiment, the device capabilities include device frequency range, maximum gain, type of ear tip fitted and/or whether the hearing device is an open or closed fit device or custom molded device.

In an embodiment, the system is arranged to communicate wirelessly with a hearing device, for example using Bluetooth or Wi-Fi protocols.

In an embodiment, the system is arranged to communicate with a hearing device through a wired connection, for example using USB protocols.

In an embodiment, the system comprises a computing device arranged to:
implement the audiogram processing component and the hearing device configuration component; and
communicate with the hearing device.

In an embodiment, the configuration data is stored in the computing device.

Alternatively or in addition, the configuration data is stored remotely of the computing device, the configuration data accessible from a networked remote location.

In an embodiment, the system is arranged to enable the computing device to download a software application arranged to implement the system when the software application is installed on the computing device.

In an embodiment, the computing device is a smartphone.

In an embodiment, the system is arranged to analyze the audiogram data to determine whether the audiogram data is representative of a medical condition that may require treatment.

In an embodiment, the system is arranged to process the audiogram data so as to compare the audiogram data with audiogram reference data, and create hearing analysis information based on the comparison, the hearing analysis information indicative of whether the audiogram data is suggestive of a hearing problem.

In an embodiment, the audiogram reference data is indicative of specific hearing conditions.

In an embodiment, the audiogram reference data is indicative of audiogram data previously obtained from the person, the system using the comparison between the audiogram data and the audiogram data previously obtained from the person in order to determine at least one trend in the person's hearing.

In an embodiment, the at least one trend includes whether significant hearing loss has occurred; whether significant hearing loss has occurred in one ear compared to the other ear; or whether a sudden onset of hearing loss, a rapidly progressing hearing loss or conductive hearing loss has occurred.

In an embodiment, the system is arranged to receive vertigo information from a user indicative that the user suffers from vertigo and to use the vertigo information and the audiogram data to diagnose a medical condition associated with the user's ears.

In an embodiment, the system is arranged to generate an alert to a user if the system determines that the audiogram data is representative of a medical condition that may require treatment.

In an embodiment, the system is arranged to validate the audiogram data by communicating with the hearing device to generate tones at levels based on the hearing thresholds defined in the audiogram data, and receiving a response from a person when the person has heard the tone. The response may be a received manually by the person physically interacting with the system or by visually recognizing an action performed by the person.

In an embodiment, the system is arranged to obtain audiogram data directly from a person by performing a hearing assessment on the person using the hearing device.

The hearing assessment may include a Hughson-Westlake process or a Modified Hughson-Westlake process and the system may be arranged to cause the hearing device to generate tones of defined frequencies and to monitor responses from the person.

In an embodiment, the system is arranged to generate audio tones corresponding to hearing thresholds consistent with the capabilities of the hearing device.

In an embodiment, the system includes at least one hearing device.

In an embodiment, the hearing device is operable in a normal mode wherein the hearing device is arranged to enhance hearing, receive streamed audio, and/or operate as a wireless headset for telephony.

In an embodiment, the hearing device is operable in a hearing assessment mode wherein a user is provided with examples of the sounds that will be presented to the user during the hearing assessment, and wherein a hearing assessment is carried out on a person.

In an embodiment, the hearing device is operable in a fitting mode wherein a user is provided with sounds to evaluate whether left and right hearing devices are properly fitted into the user's ears.

In an embodiment, the system is arranged such that during a hearing assessment, the hearing device restricts or prevents functionality of hearing device, for example so as to not allow reception of incoming calls, user input from controls on the hearing device, or reception of streamed audio, such as music.

In an embodiment, the hearing device is arranged to remain in hearing assessment mode while a hearing assessment process is active, and to switch to normal mode if a hearing assessment process is inactive. The system may be arranged to repeatedly poll the hearing device, and the hearing device arranged to switch to normal mode if a poll communication is not received after a defined period of time.

In an embodiment, during a hearing assessment, the tones include a pure tone, a pulsed tone, a warble tone, a pulsed warble tone, band limited noise or any other suitable sound for use during a hearing assessment.

In an embodiment, during a hearing assessment, the system is arranged to generate sound generation commands and to send the sound generation commands to the hearing device, each sound generation command usable by the hearing device to create sound associated with the command.

In an alternative embodiment, during a hearing assessment, the system is arranged to stream sounds to the hearing device.

In an embodiment, the hearing device is arranged to assess the level of background ambient noise and determine whether the level of background ambient noise is sufficiently low to carry out a hearing assessment. The hearing device may comprise at least one microphone, the hearing device using the microphone to assess the level of background ambient noise.

In an embodiment, the system is arranged to generate a low frequency tone and to assess whether the hearing device is properly fitted into a user's ear by determining whether the user has heard the low frequency tone. The low frequency tone may be a continuous tone, a pulsed tone, a pulsed warble tone or a heartbeat tone.

In an embodiment, the system is arranged to display a hearing results indicator, the hearing results indicator communicating graphically the hearing characteristics of a person associated with audiogram data.

The hearing results indicator may include a left ear portion including graphical information associated with hearing capabilities of the person in a left ear, and a right ear portion including graphical information associated with hearing capabilities of the person in a right ear. The right and left ear portions may correspond to hemispheres of a circle.

In an embodiment, each ear portion includes multiple concentric ring portions, each ring portion corresponding to a different frequency used in the hearing assessment.

In an embodiment, the length of each ring portion corresponds to the strength of hearing at the frequency associated with the ring portion. The ring portions may be represented differently based on whether the ring portions are associated with the left or right ear, for example by displaying the ring portions in different colours, and may be represented differently based on the relevant frequency, for example by displaying the ring portions for each ear in different shades of the same colour.

In an embodiment, the system is arranged to facilitate editing of the audiogram data. The system may be arranged to display a visual representation of the audiogram data, and to enable a person to modify the visual representation and thereby the audiogram data.

In an embodiment, the system is arranged to allow a person to modify the configuration data either directly or indirectly. The modifications may be carried out while the hearing device is being worn.

The modifications may include modification of a gain, feedback response, frequency response, compression parameter or other parameters such as tinnitus related parameters.

During modification, the hearing device configuration data may be updated on the hearing device on-the-fly so that a wearer of the hearing device can hear changes as they are being made.

Also disclosed is a system for configuring a hearing device, the system comprising:
  audiogram data indicative of an audiogram associated with a person;
  a hearing device configuration component arranged to produce hearing device configuration data based on the audiogram data, the configuration data indicative of configuration settings for a hearing device that will cause the hearing device to assist the hearing of the person; and
  an audiogram data analysis component arranged to analyse the audiogram data to determine whether to communicate recommendation information to the person, the recommendation information indicative of a recommendation to carry out a hearing related action;
  the system arranged to communicate the recommendation information to the person if the determination is affirmative.

In an embodiment, the recommendation information is indicative of a referral to a health professional.

In an embodiment, the audiogram data analysis component is arranged to retrieve the recommendation information from a referral database.

In an embodiment, the audiogram data analysis component is arranged to retrieve the recommendation information based on defined criteria, for example based on locality.

In an embodiment, the system includes a location device arranged to produce location information indicative of the location of the system, and the system is arranged to use the location information to select recommendation information indicative of a referral to a health professional based on the location of the professional.

In an embodiment, the system is arranged to compare a user's electronic calendar with an accessible electronic calendar of a selected hearing health professional so that a mutually free timeslot for the user and the hearing health professional can be identified.

In an embodiment, the audiogram data analysis component is arranged to analyse the audiogram data with reference to capabilities of a hearing device associated with a person, and to determine whether the capabilities of the hearing device are suitable for the hearing capabilities of the person defined in the audiogram data, and the system is arranged to communicate recommendation information indicative of a different hearing device if the different hearing device has more suitable capabilities than the hearing device associated with the person.

In an embodiment, the recommendation information may be displayed to the person and/or electronically communicated to one or more relevant people.

Also disclosed is a system for configuring a hearing device, the system comprising:
  an audiogram creation component arranged to produce audiogram data associated with a person by causing a hearing assessment to be performed on the person using the hearing device, the hearing assessment including generation of sounds of defined frequencies and recording responses from the person; and
  a hearing device configuration component arranged to produce hearing device configuration data based on the audiogram data, the configuration data indicative of configuration settings for a hearing device that will cause the hearing device to assist the hearing of the person.

Also disclosed is a method of configuring a hearing device, the method comprising:
  processing image data indicative of an image of an audiogram associated with a person so as to produce audiogram data indicative of the audiogram;
  producing hearing device configuration data based on the audiogram data, the configuration data indicative of configuration settings for a hearing device that will cause the hearing device to assist the hearing of the person;
  obtaining information indicative of the capabilities of the hearing device; and
  producing configuration data using the information indicative of the device capabilities of the hearing device.

Also disclosed is a hearing assistance system comprising:
  a hearing assistance device configured to reproduce sounds and to assist a person to hear the sounds; and
  a computing device in communication with the hearing assistance device;
  the computing device including a processor configured to implement a hearing device configuration component that configures the hearing assistance device for the person;
  the hearing device configuration component interacting with the hearing assistance device to:
    implement a hearing assessment on the person using the hearing assistance device, the hearing assessment including generation of hearing assessment sounds of defined frequencies at the hearing assistance device and recording responses from the person; and
    configure the hearing assistance device using the responses from the person;
  the hearing device configuration component producing hearing assessment sound generation commands and sending the sound generation commands to the hearing assistance device; and
  the hearing assistance device configured to use the sound generation commands to generate the hearing assessment sounds during the hearing assessment.

Also disclosed is a hearing assistance system comprising:
a hearing assistance device configured to reproduce sounds and to assist a person to hear the sounds; and
a computing device in communication with the hearing assistance device;
the computing device including a processor configured to implement a hearing device configuration component that configures the hearing assistance device for the person;
the hearing device configuration component interacting with the hearing assistance device to:
implement a hearing assessment on the person using the hearing assistance device, the hearing assessment including generation of hearing assessment sounds of defined frequencies at the hearing assistance device and recording responses from the person; and
configure the hearing assistance device using the responses from the person;
wherein the system is configured to assess the level of background ambient noise prior to implementation of a hearing assessment and determine whether the level of background ambient noise is sufficiently low to carry out the hearing assessment.

In accordance with a first aspect of the present invention, there is provided a hearing assistance system comprising:
a hearing assistance device configured to reproduce sounds and to assist a person to hear the sounds, the hearing assistance device including a left hearing assistance device and a right hearing assistance device; and
a computing device in communication with the hearing assistance device;
the computing device interacting with the hearing assistance device to implement a fitting mode wherein the hearing assistance device is caused to generate fitting sounds usable to evaluate whether the left and right hearing devices are properly fitted into respective left and right ears of the person; and
the computing device producing a communication indicative of whether the left and right hearing assistance devices are properly fitted into respective left and right ears of the person.

In accordance with a second aspect of the present invention, there is provided a hearing assistance system comprising:
a hearing assistance device configured to reproduce sounds and to assist a person to hear the sounds; and
a computing device in communication with the hearing assistance device;
the computing device including a processor configured to implement a hearing device configuration component that configures the hearing assistance device for the person;
the hearing device configuration component interacting with the hearing assistance device to:
implement a hearing assessment on the person using the hearing assistance device, the hearing assessment including generation of hearing assessment sounds of defined frequencies at the hearing assistance device and recording responses from the person; and
configure the hearing assistance device using the responses from the person;
wherein the system is configured to restrict or prevent defined functionality of the hearing assistance device during the hearing assessment.

In accordance with a third aspect of the present invention, there is provided a hearing assistance system comprising:
a hearing assistance device configured to reproduce sounds and to assist a person to hear the sounds; and
a computing device in communication with the hearing assistance device;
the computing device including a processor configured to implement a hearing device configuration component that configures the hearing assistance device for the person;
the hearing device configuration component interacting with the hearing assistance device to:
implement a hearing assessment on the person using the hearing assistance device, the hearing assessment including generation of hearing assessment sounds of defined frequencies at the hearing assistance device and recording responses from the person; and
configure the hearing assistance device using the responses from the person;
wherein the system is arranged to generate hearing assessment sounds consistent with the capabilities of the hearing assistance device.

Also disclosed is a method of configuring a hearing assistance device comprising:
providing a hearing assistance device configured to reproduce sounds and to assist a person to hear the sounds;
connecting the hearing assistance device in communication with a computing device;
implementing a hearing assessment on the person using the hearing assistance device by:
producing hearing assessment sound generation commands at the computing device, the hearing assessment sound generation commands indicative of hearing assessment sounds of defined frequencies;
sending the sound generation commands from the computing device to the hearing assistance device;
generating hearing assessment sounds at the hearing assistance device using the sound generation commands; and
recording responses from the person to the generated hearing assessment sounds; and
configuring the hearing assistance device using the responses from the person.

BRIEF DESCRIPTION OF THE DRAWINGS

The present invention will now be described, by way of example only, with reference to the accompanying drawings, in which.

DESCRIPTION OF AN EMBODIMENT OF THE INVENTION

Figure 1:
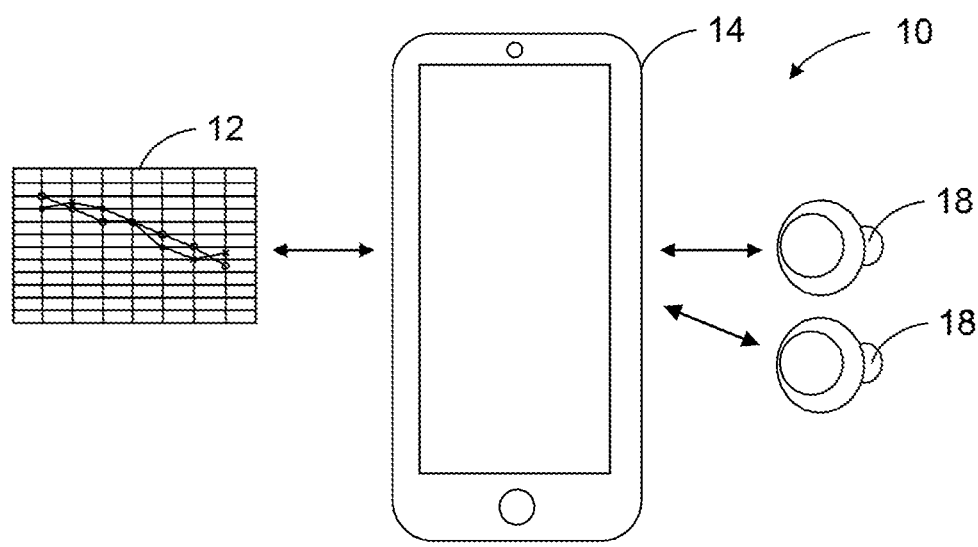
FIG. 1 is a diagrammatic representation of a system for configuring a hearing device in accordance with an embodiment of the present invention.

Referring to FIG. 1 of the drawings, there is shown a representation of an embodiment of a system 10 for configuring a hearing device.

During use, the system is arranged to capture an image 12 of an audiogram using a computing device, in this example a smartphone 14 provided with a camera 16, and to process the captured audiogram image so as to produce configuration data indicative of configuration settings for a hearing device 18 that will cause the hearing device to assist the hearing of a person associated with the audiogram. In this way, a hearing device 18 can be specifically configured for a person's hearing capabilities by using the audiogram associated with the person to automatically modify settings of the hearing device 18 to suit the person.

Importantly, configuration of the hearing device 18 can be achieved by a person without the need for the person to have any technical expertise in relation to audiograms and/or in relation to configuration of the hearing device 18.

It will be understood that the system 10 may be implemented using any suitable computing device capable of executing programs, displaying information to a user and receiving inputs from the user. For example, the computing device may be of portable type that includes a touch screen capable of receiving inputs from a user, or a personal computer having a keyboard and mouse.

In this example, the computing device is a smartphone 14 arranged to communicate wirelessly with the hearing device 18, in this example a pair of left and right hearing devices 18, for example using a Bluetooth or WiFi communication protocol, although it will be understood that any suitable communications arrangement is envisaged.

Figure 2:
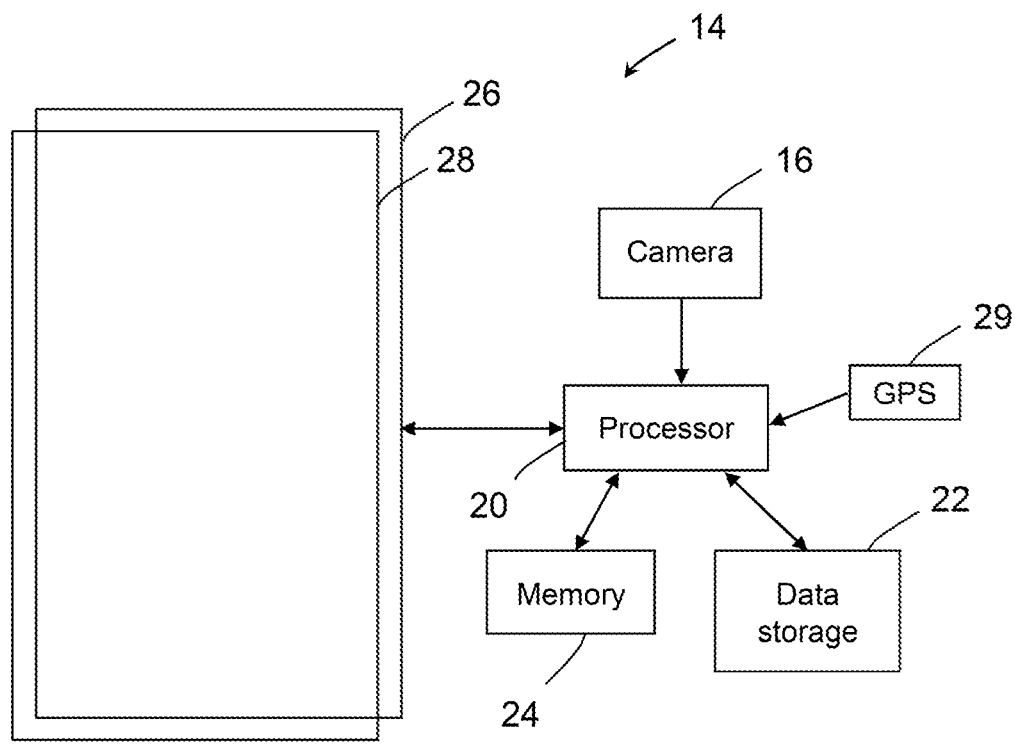
FIG. 2 is a schematic block diagram of a smartphone for use in the system shown in FIG. 1.

As shown in FIG. 2, the smartphone 14 includes a camera 16, and a processor 20 arranged to implement programs stored in a data storage device 22 using memory 24 in order for the smartphone to implement desired functionality of the system 10. The smartphone 14 also includes a touch screen 28 overlaid on a display device 26. As such, inputs are primarily effected by touching the touch screen using taps, swipes and any other device recognizable gestures. The smartphone 14 also includes a location device arranged to produce location information indicative of the location of the smartphone, in this example a GPS device 29. However, it will be understood that the system 10 is equally applicable to implementations on other computing devices.

Figure 3:
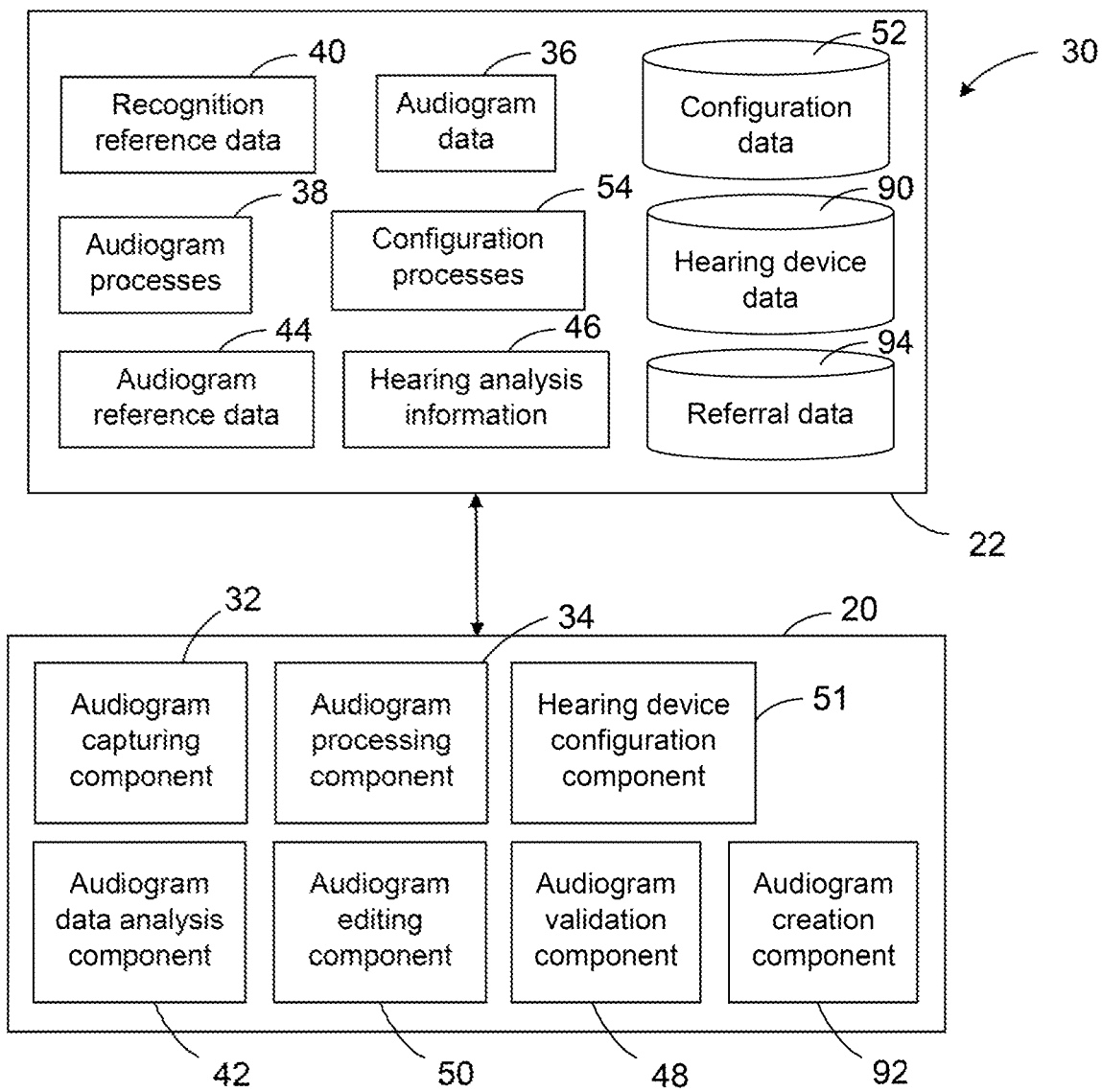
FIGS. 3 and 4 show block diagrams of functional components of the system shown in FIGS. 1 and 2.

Referring to FIG. 3, a block diagram is shown of functional components 30 of the system 10. The functional components 30 in this example include process components implemented by the processor 20; and system data stored in the data storage device 22, the system data including data indicative of processes implemented by the processor 20 and data usable by and produced by the processes implemented by the processor 20.

In this example, the functional components 30 include an audiogram capturing component 32 arranged to facilitate capture of an audiogram associated with a person using the camera 16; an audiogram processing component 34 arranged to process the captured audiogram to produce audiogram data 36 indicative of the captured audiogram; an audiogram data analysis component 42 arranged to analyze the audiogram data 36 in order to determine the likelihood of a medical issue; an audiogram validation component 48 arranged to cooperate with the hearing device 18 to validate the audiogram data 36; an audiogram editing component 50 arranged to facilitate editing of the audiogram data 36, for example in order to ensure that the audiogram data 36 accurately represents the audiogram; and a hearing device configuration component 51 arranged to generate configuration data 52 and to communicate with the hearing device 18 in order to configure the hearing device 18 for a person according to the audiogram associated with the person.

In a variation, the functional components 30 may also include an audiogram creation component 92 arranged to facilitate creation of audiogram data 36 for a person directly using the system 10 by implementing a hearing test with the person using the hearing device 18, and without deriving the audiogram data 36 from an audiogram.

In order to implement the system 10 using the smartphone 14, a prospective user first downloads a software application associated with the system from a suitable software repository onto the user's smartphone 14 and installs the software application on the smartphone 14, the software application arranged to implement the functional components 30 shown in FIG. 3.

Figure 4:
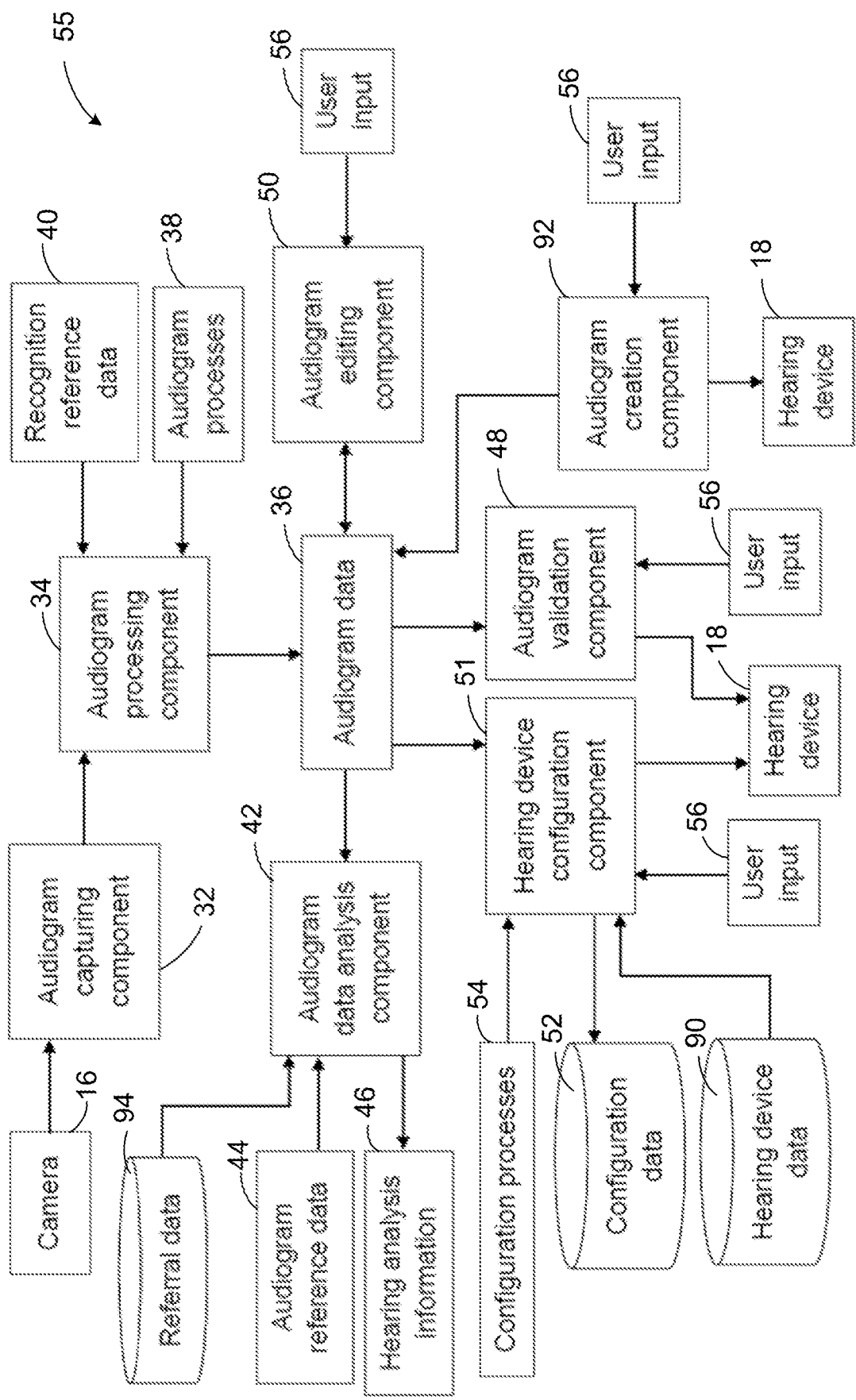

Referring to FIG. 4, a functional diagram 55 is shown illustrating the functional components 30 of the system 10 and interactions between the functional components 30 during operation of the system 10.

An example of the system 10 during use will now be described in relation to a smartphone 14, wherein data used by and generated by the system 10 is stored in the data storage device 22 of the smartphone 14.

Figure 5:
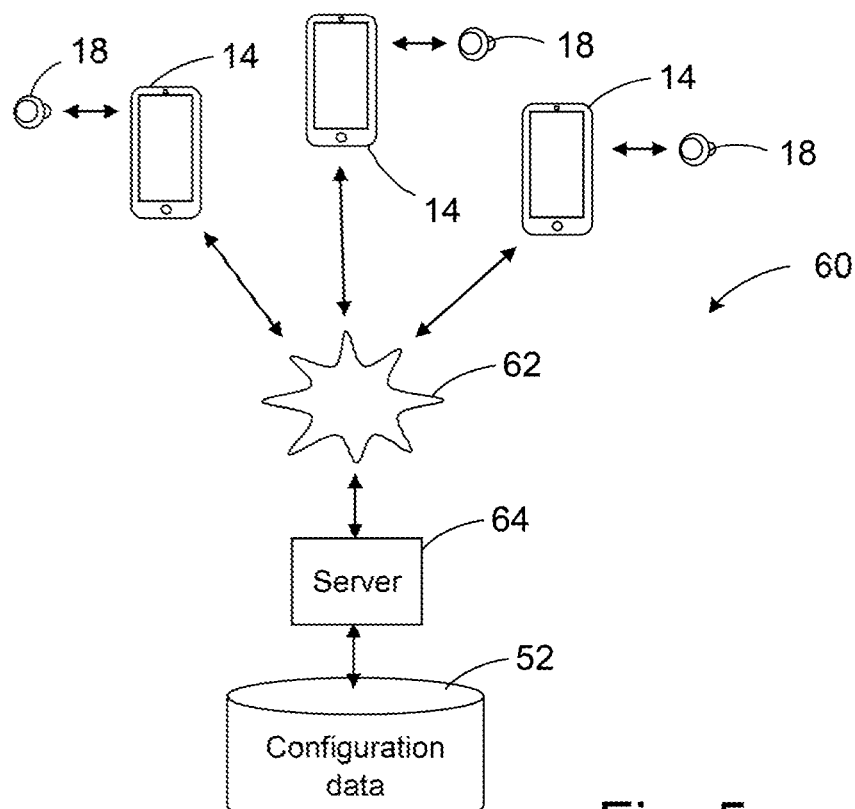
FIG. 5 is a diagrammatic representation of an alternative system for configuring a hearing device in accordance with an embodiment of the present invention.

However, it will be understood that other arrangements are possible. For example, at least some data used by and produced by the system 10 may be obtained from or stored remotely from the smartphone 14. In an example implementation 60 shown in FIG. 5, multiple computing devices, in this example multiple smartphones 14, communicate through a network such as the Internet 62 with a remote server 64 in order to store configuration data 52 associated with audiograms. In this way, the configuration data 52 particular to each person associated with the system is stored in a common accessible location so that the relevant current configuration data can be obtained and used to configure or reconfigure a hearing device 18 using any computing device.

Figure 6:
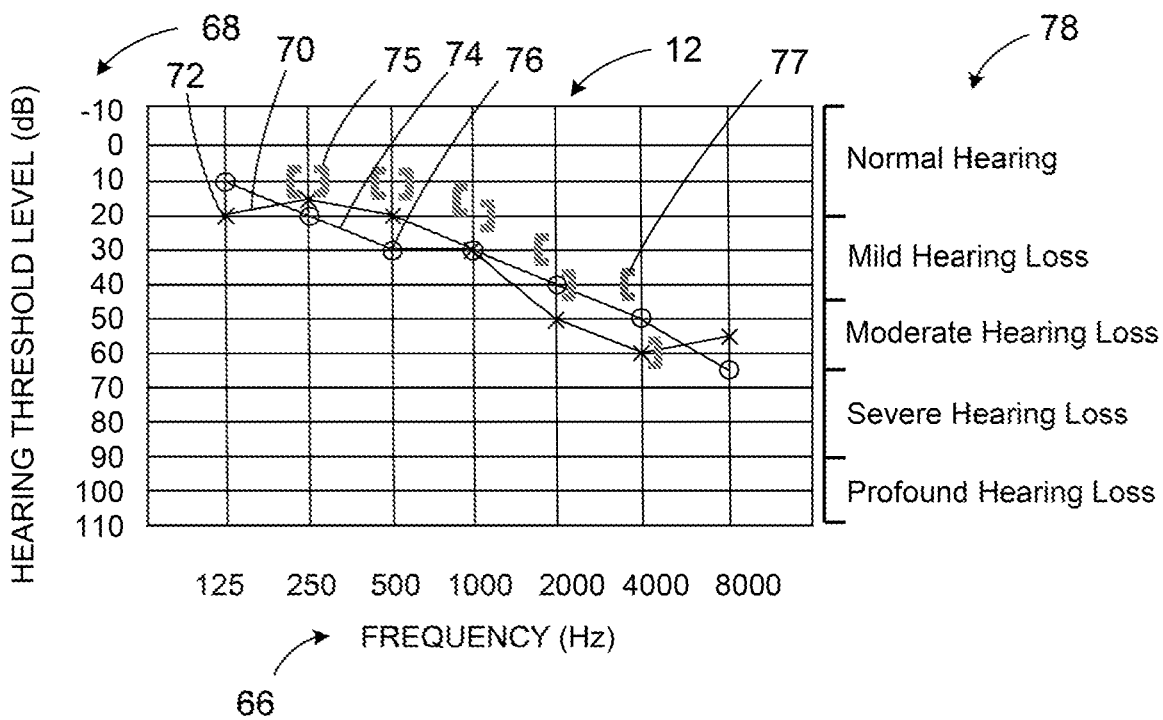
FIG. 6 shows an example audiogram.
Figure 7:
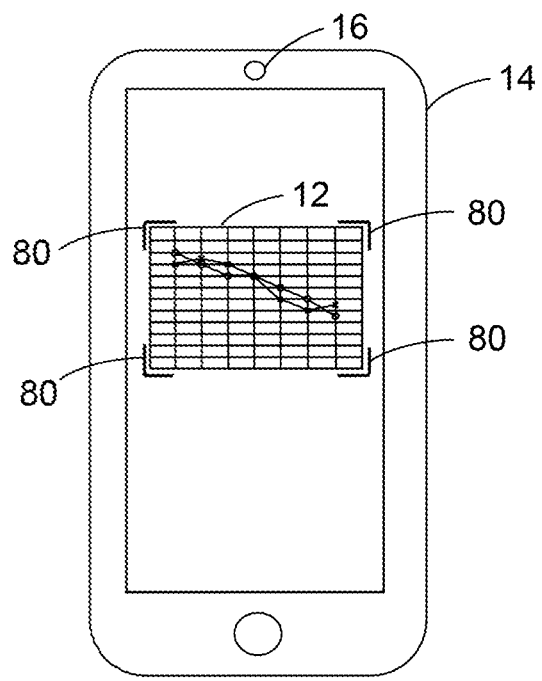
FIG. 7 shows a smartphone during capture of an image of an audiogram.

An example audiogram 12 is shown in FIG. 6.

An audiogram 12 is a representation of characteristics of a person's hearing ability, in this example in visual form, and includes a frequency x-axis 66, a hearing threshold level y-axis 68, a left ear air conduction plot 70 having left ear symbols 72, and a right ear air conduction plot 74 having right ear symbols 76. Each of the plots 70, 74 represents the air conduction hearing characteristics of an ear of a person at particular frequencies, in this example at 125 Hz, 250 Hz, 500 Hz, 1 kHz, 2 kHz, 4 kHz and 8 kHz, in terms of hearing thresholds of the person at the particular frequencies. The audiogram 12 also includes left ear bone conduction symbols 75 and right ear bone conduction symbols 77 that represent the bone conduction hearing characteristics of ears of a person at particular frequencies, in this example at 250 Hz, 500 Hz, 1 kHz, 2 kHz and 4 kHz. An audiogram typically uses red 'O' symbols for right ear air conduction hearing thresholds, blue 'X' symbols for left ear air conduction hearing thresholds, ']' symbols for right ear bone conduction hearing thresholds, and '[' symbols left ear bone conduction hearing thresholds, although it will be understood that other colours and symbols may be used to represent these or other thresholds or information present on the audiogram.

In the example audiogram 12 shown in FIG. 6, the person has abnormal hearing in both left and right ears at frequencies above 500 Hz, and therefore the person represented in the audiogram 12 would benefit from some hearing assistance that could be provided by a hearing device 18 appropriately configured for the person's hearing capabilities.

In an example during use a person has obtained an audiogram 12 from a health professional that represents the hearing capabilities of the person, and in particular any hearing difficulties that the person has, and the person wishes to program his/her hearing device 18 according to the hearing characteristics defined in the audiogram 12.

Referring to FIG. 4, the person first captures the audiogram 12, in this example using the camera 16 of the person's smartphone 14. In this example, the audiogram 12 is printed on paper and capture of an image of the audiogram 12 is achieved using the smartphone 14 by aligning the printed audiogram 12 with an image capture frame 80 using conventional touch inputs including zoom and rotate touch gestures. Image capture is implemented using the audiogram capturing component 32 according to one or more associated processes stored in the data storage device 22.

In an alternative embodiment, the system is arranged to receive image data indicative of an audiogram through a communications link, for example using USB, Bluetooth or Wi-Fi protocols. In this way, the image data indicative of an audiogram may be captured by the system by importing the image data over a network or by importing the image data from a portable data storage device such as a USB drive.

After capture of the audiogram 12, the audiogram is processed by the audiogram processing component 34 in order to recognise relevant hearing characteristic data in the audiogram 12 and produce audiogram data 36 that is indicative of the hearing characteristics of the person associated with the audiogram 12, in particular the hearing threshold levels at specific frequencies. The audiogram processing component 34 implements one or more audiogram processes 38 in order to obtain the audiogram data 36 from the audiogram image, for example a template matching and phase correlation process to identify the positions and locations of the left and right ear symbols in the audiogram image and the x-axis and y-axis scales, and a translation process to translate the audiogram image into the audiogram data 36. The audiogram processes 38 may use recognition reference data 40 stored in the data storage device 22 that for example represents reference audiograms for which audiogram data is known.

Template matching may be performed by creating templates for air conduction hearing threshold markers, bone conduction hearing threshold markers and other symbols found in a typical audiogram, such as those specified in ANSI standard 53.21. In this example, templates are formed for X, O, [and] symbols representing the hearing thresholds in the audiogram. A further template is also created for the grid structure used in the audiogram.

Optical character recognition or template matching to character symbols representing the dB scale may be used to determine reference points for dB levels in the audiogram data. Similarly, optical character recognition or template matching to character symbols representing the frequency scale may be used to determine reference points for frequency points in the audiogram image.

The templates are convolved with the audiogram image at all possible pixel locations in the image, and the result compared to a threshold to determine the likely location of the symbols in the image. This is repeated for all templates to identify the location of the grid structure, the air conduction hearing thresholds and the bone conduction thresholds. Further this process can also be repeated to determine the location of dB markings and frequency markings in the audiogram image.

After the locations of the relevant items on the audiogram image have been identified, the audiogram image data can be translated to audiogram data.

The audiogram processes 38 may employ other techniques, including support vector machines or artificial neural networks that use recognition reference data 40 as training data for the neural network. In an example, the training data consists of many, typically 1000 or more, audiogram images with corresponding audiogram data 36 that has been generated by a human operator. The training data is used to develop models that can then be used by the audiogram processing component 34 to generate the audiogram data 36.

The audiogram data 36 may be indicative of numerical data that identifies a hearing threshold in dB at specific frequencies 125 Hz, 250 Hz, 500 Hz, 1 kHz, 1.5 kHz, 2 kHz, 3 kHz, 4 kHz, 6 kHz and 8 kHz, with the hearing thresholds identified between 0 dB and 120 dB in 5 dB increments.

The audiogram 12 may also indicate bone conduction measurements, air conduction measurements, masked measurements or other measurements (not shown) that can also be identified by the audiogram capturing component 32 and included in the audiogram data 36 for analysis by the audiogram processing component 34. This would allow for more accurate tuning of the hearing device for hearing assistance purposes.

In addition, the present system 10 is also arranged to enable audiogram data to be obtained directly from a person using the hearing device 18.

In this embodiment, the audiogram data 36 may be processed by the audiogram data analysis component 42 so as to compare the audiogram data with a database of existing audiogram reference data 44, and create hearing analysis information 46 on the basis of the comparison, for example for storage in the data storage device 22. The hearing analysis information 46 may provide the person associated with the audiogram data 36 with an indication as to whether the audiogram data 36 is suggestive of a hearing problem.

For example, the audiogram data analysis component 42 may compare the audiogram data 36 currently obtained from a person with reference audiogram data 44, for example indicative of specific hearing or other medical conditions. Alternatively, the audiogram data analysis component 42 may compare the audiogram data 36 currently obtained from the person with previously produced audiogram data 44 for the person in order to determine trends in the person's hearing, such as whether significant hearing loss has occurred; whether significant hearing loss has occurred in one ear compared to the other ear; whether a sudden onset of hearing loss, a rapidly progressing hearing loss or conductive hearing loss has occurred; and so on.

The system may also be arranged to receive vertigo information from a user indicative that the user suffers from vertigo and to use the vertigo information and the audiogram data to diagnose a medical condition associated with the user's ears.

If the system determines that a medical problem may be present, the system may be arranged to generate an alert to a user, for example in the form of a visible and/or audible alert.

In this embodiment, the audiogram data 36 may be used by the audiogram validation component 48 to validate the audiogram data 36 with the person associated with the audiogram data 36 by communicating with the hearing device 18 to play tones at levels based on the hearing thresholds defined in the audiogram data 36. For example, the system 10 may cause the hearing device 18 to play tones at or close to the hearing thresholds defined in the audiogram data 36. The person is then required to indicate if the tone has been heard, for example using the touch screen to provide a user input 56 or by performing a gesture that is visually recognised by the system. If no tone is heard at a hearing threshold defined in the audiogram data 36, this may indicate that the audiogram data 36 has been incorrectly generated from the audiogram image or the audiogram itself should be updated by carrying out a new hearing test. The test may use the Hughson-Westlake procedure or the modified Hughson-Westlake procedure, with a starting hearing threshold set at an additional 15 dB starting intensity level. If the results of the validation do not align to the audiogram data 36, for example within +/−10 dB, then the system may be arranged to generate an alert, for example displayed on the display 26 of the smartphone 14.

In this embodiment, the person has an opportunity to edit the audiogram data 36 produced by the audiogram processing component 34, for example if required in order to correct an error in the audiogram process(es) 38 carried out by the audiogram processing component 34.

Figure 8:
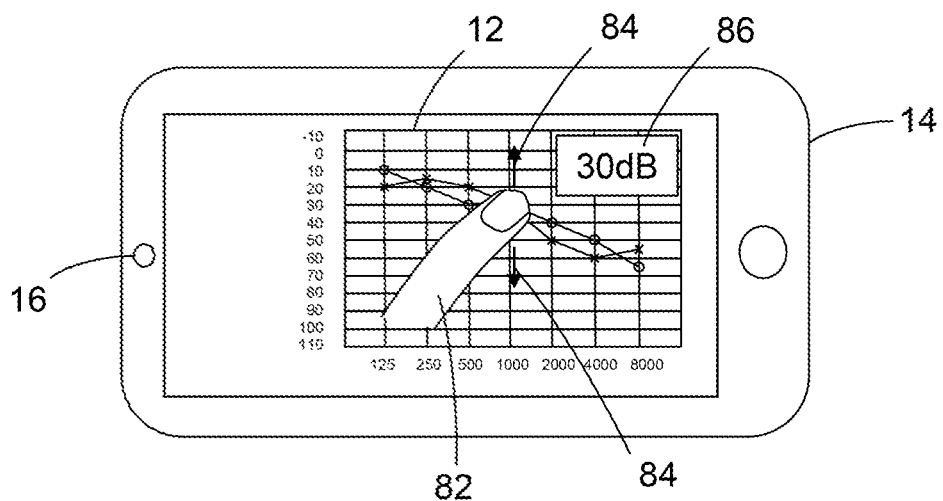
FIG. 8 shows a smartphone during editing of a captured audiogram image.

For example, as shown in FIG. 8, a person may view a visual representation of the audiogram data 36 and interact with the visual representation in order to move one or more left and/or right symbols if one or more of the symbols are incorrectly located. The person may for example interact with the visual representation using a finger 82, and may for example correct a symbol location by touching the incorrect symbol location and moving the symbol to a correct location in the direction of one of the arrows 84. In this example, a decibel indicator 86 is also provided to visually display the current location in decibels of a symbol touched by the person.

Using the audiogram data 36, the hearing device configuration component 51 applies one or more configuration processes 54, for example stored in the data storage device 22, to the audiogram data 36 to produce configuration data 52 usable by the hearing device 18 to program the hearing device and thereby improve the hearing of the person.

Additional configuration information may be required in order to configure the hearing device 18, including information indicative of the age and sex of the person, whether the person is an experienced hearing device user, and/or the primary language of the hearing device user. The additional configuration information may be received from a person, for example the intended user of the hearing device 18.

The configuration processes may include processes arranged to use formulae NAL-R, NAL-NL1, NAL-NL2 or other processes such as DSLv5 to generate hearing device configuration data 52 from the audiogram data 36, or any other process suitable to produce configuration data 52 from the audiogram data 36. The hearing device configuration component 51 may also produce configuration data 52 in consideration of the performance capabilities of the hearing device 18.

For example, for the audiogram example shown in FIG. 6, the audiogram processing component 34 generates audiogram data 36 as shown in Table 1 below.

TABLE 1

| Frequency/Hz | Left Air Conduction Threshold | Right Air Conduction Threshold |
|---|---|---|
| 125 | 20 | 10 |
| 250 | 15 | 20 |
| 500 | 20 | 30 |
| 1000 | 30 | 30 |
| 2000 | 50 | 40 |
| 4000 | 60 | 50 |
| 8000 | 55 | 65 |

For example, using a NAL-R prescription formula the audiogram data can then be translated into hearing device configuration data corresponding to frequency bands 250 Hz, 500 Hz, 1000 Hz, 2000 Hz and 4000 Hz, as shown in Table 2 below.

TABLE 2

| Frequency/Hz | Left Ear Gain | Right Ear Gain |
|---|---|---|
| 250 | −7.35 | −5.8 |
| 500 | 3.2 | 6.3 |
| 1000 | 15.3 | 15.3 |
| 2000 | 19.5 | 16.4 |
| 4000 | 21.6 | 18.5 |

The NAL-R formula is:

$$H_{3FA}=(H_{500}+H_{1k}+H_{2k})/3$$

$$X=0.15 H_{3FA}$$

$$IG_i = X + 0.31 H_i + k_i$$

where $H_i$ is a hearing threshold value specified in the audiogram data 36, $IG_i$ is the gain value ('insertion gain') used to program the hearing device 18, and $k_i$ is determined according to Table 3.

TABLE 3

| Frequency/Hz | $K_i$/dB |
|---|---|
| 250 | −17 |
| 500 | −8 |
| 1000 | 1 |
| 2000 | −1 |
| 3000 | −2 |
| 4000 | −2 |
| 6000 | −2 |

The performance capabilities of the hearing device 18 may be obtained by querying the device for its capabilities, or by obtaining the capabilities from a local 90 or remote (not shown) hearing device database, for example connected in networked communication with the system 10. In a variation, the system may be arranged to query the hearing device 18 in order to obtain identification information indicative of the type of hearing device 18, such as a serial number of the hearing device 18, and to use the identification information to retrieve the device capabilities associated with the hearing device 18, for example from a local or remote storage device.

Such device capabilities may include device frequency range, maximum gain, type of ear tip fitted and whether the hearing device is an open or closed fit device. The hearing device capabilities may also be entered manually.

Communication between the smartphone 14 and the hearing device 18 can occur through a common communication established using a wired or wireless connection that may use Bluetooth, Wi-Fi or USB protocols.

Using the communication link between the smartphone 14 and the hearing device 18, the system is able to configure the hearing device 18 according to the configuration data 52 produced for the person.

The communication link may also be used to query the hearing device 18 for device capabilities or status information, and allows transmission of current configuration data stored on the hearing device 18 from the hearing device 18 to the smartphone 14 in order to allow the configuration data to be reviewed and modified as required. The configuration data obtained from the hearing device 18 may be stored on the smartphone 14.

The communication link may also be used to obtain hearing device specific information, such as the serial number associated with the hearing device.

The system 10 may also be arranged to allow a person to fine tune the configuration of the hearing device 18 by modifying the configuration data 52 either directly or indirectly. Such modifications may be carried out while the hearing device 18 is being worn, and the wearer may provide verbal feedback, touch feedback or otherwise.

Information indicative of the modification(s) may then be displayed on the display 26 of the smartphone 14. The system may also provide audible feedback through the hearing device 18 or a separate speaker.

Fine tuning may include modification of a gain, feedback response, frequency response, compression parameters or any other configuration parameter associated with the hearing device 18. During fine tuning, the hearing device configuration data may be updated on the hearing device 18 in a live manner so that the wearer of the hearing device 18 can hear changes as they are being made. After confirming that the modifications are acceptable, the hearing device configuration component 51 updates the configuration data 52 stored at the smartphone 14 and on the hearing device 18.

The hearing device 18 may also store data and usage statistics such as environmental information or listening situations in which the hearing device 18 has been used.

In addition to deriving audiogram data 36 from an image of an audiogram, the audiogram data 36 may be obtained for a person by performing a hearing assessment on the person using the hearing device 18. For example, if an audiogram for the person is not available, or at the election of the user, the following hearing assessment process may be implemented using the audiogram creation component 92.

Initially, the person may be directed to wear the hearing device 18, for example by providing an audible or visible prompt to the person. The audiogram creation component 92 then interacts with the hearing device 18 to undertake a hearing assessment, for example a Hughson-Westlake process or a Modified Hughson-Westlake process, to measure hearing threshold data associated with the user by causing the hearing device 18 to generate sounds of particular frequencies and monitoring responses to the sounds, for example received using the touch screen 28.

The Hughson-Westlake process and Modified Hughson-Westlake process can be time consuming and require a person's attention and concentration for extended periods of time. The time required to complete the process can be significantly reduced by only obtaining hearing threshold data relevant to the capabilities of the audio device 18. For example, the process may be modified to only present audio tones corresponding to hearing thresholds consistent with the audio device fitting range. Audio tones should however also be presented that correspond to hearing thresholds outside of the device fitting range, for example corresponding to +/−10 dB.

The Hughson-Westlake process and Modified Hughson-Westlake process can be administered in an automatic programmatic way by the audiogram creation component 92 by causing the hearing device 18 to present audio stimuli and monitoring user feedback that indicates whether the audio stimuli have been heard.

In this example, the audiogram creation component 92 is arranged to test for hearing threshold levels at frequency points 125 Hz, 250 Hz, 500 Hz, 1000 Hz, 1500 Hz, 2000 Hz, 3000 Hz, 4000 Hz, 6000 Hz and 8000 Hz, although it will be understood that any suitable frequency points are envisaged. For example, the number of frequency points can be reduced if a shorter test is desired, such that only frequency points 500 Hz, 1000 Hz, 2000 Hz and 4000 Hz are used.

Also in this example, the audiogram creation component 92 is arranged to increase the audio stimuli at 5 dB increments, although it will be understood that any suitable increment is envisaged.

The process may require the user's better ear to be assessed first, for example determined according to user input. If no better ear is indicated, the left ear may be assessed first.

An example of an arrangement for performing a hearing assessment on a person using the hearing device 18 will now be described with reference to FIGS. 9 to 25. The hearing assessment is carried out directly using the hearing device 18 under control of the computing device, in this example a smartphone 14. It will be understood that in order to provide the required functionality on the smartphone 14, a dedicated software application is installed on the smartphone 14, for example obtained from an online software repository. The software application may be part of the software application arranged to implement the functional components 30 shown in FIG. 3 or may be a separate application.

In this example, the hearing device 18 is operable in 3 modes:
- a normal mode wherein the hearing device 18 is arranged to enhance hearing, receive streamed audio from a computing device such as a smartphone, and operate as a wireless headset for telephony;
- a fitting mode wherein sounds are presented to the user and an assessment is made as to whether left and right hearing devices are properly fitted into the user's ears; and
- a hearing assessment mode wherein a hearing assessment is carried out by the left and right hearing devices with the computing device, in this example the smartphone 14.

During the fitting mode and the hearing assessment mode, the hearing device 18 does not allow reception of incoming calls, user input from controls on the hearing device 18, or reception of streamed audio, such as music, from the computing device 14. In addition, while sound from microphones on the hearing device may be processed, the sound received at the microphones is not reproduced by the hearing device speakers during the fitting mode and the hearing assessment mode.

In the present embodiment, the hearing device 18 is arranged to remain in fitting mode or hearing assessment mode while a hearing assessment process is active, and in this example the smartphone 14 is arranged to repeatedly poll the left and right hearing devices 18 while the hearing assessment application on the smartphone 14 is active. If the hearing devices 18 do not receive a poll communication from the smartphone 14 after a defined period of time, the hearing devices 18 are arranged to switch back to normal mode as, for example, it is assumed that the smartphone application has been closed.

Figure 9:
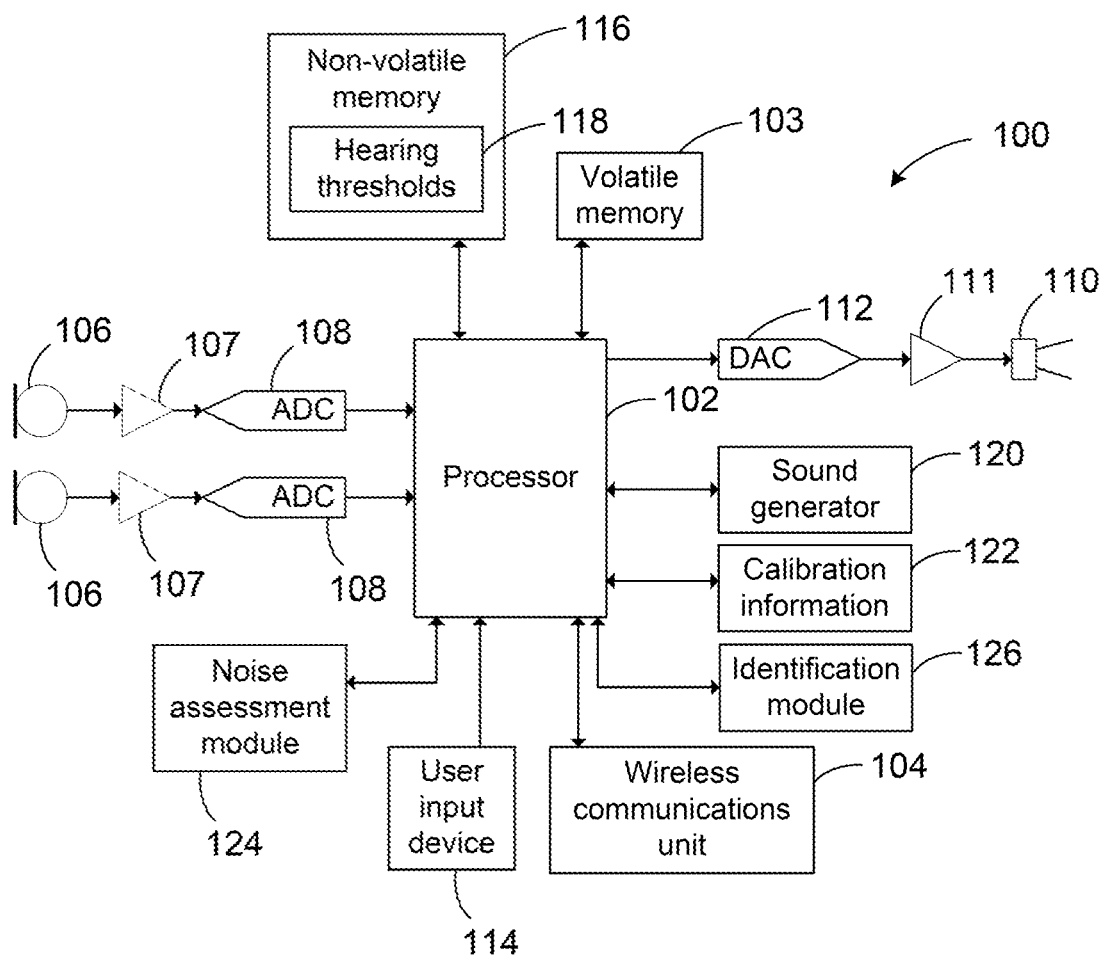
FIG. 9 is a schematic block diagram of a hearing device of the system shown in FIG. 1.

Referring to FIG. 9, functional components 100 of the hearing device 18 are shown schematically.

The functional components 100 include a processor 102 arranged to control and coordinate operations in the hearing device 18, and a volatile memory 103 used by the processor to implement programs associated with functionality of the hearing device 18.

The functional components 100 also include a wireless communications unit 104 arranged to facilitate wireless communication to and from the hearing device, in particular between the hearing device 18 and a computing device such as a smartphone 14. In this example, the wireless communications unit 104 is arranged to support Bluetooth communications, Bluetooth low energy communications and/or WiFi communications, although it will be understood that any suitable communications protocol is envisaged.

In an embodiment, the smartphone 14 is arranged to communicate with both left and right hearing devices 18. Alternatively, the smartphone 14 is arranged to communicate with one of the left and right hearing devices 18 as a master hearing device, with the master hearing device communicating directly with the other hearing device as a slave hearing device.

The functional components 100 also include several, in this example 2, microphones 106, each microphone 106 having an associated amplifier 107 and analogue to digital converter 108. The microphones 106 are arranged to receive sound information associated with the ambient environment and for example the system may use the received sound information to determine the ambient noise level.

The functional components 100 also include a speaker 110 having an associated amplifier 111 and digital to analogue converter 112. The speaker 110 is arranged to produce sound corresponding to sound information provided by the processor 102. In this example, during a hearing assessment, the sound may comprise tones including a pure tone, a pulsed tone, a warble tone, a pulsed warble tone, band limited noise or any other suitable sound for use during a hearing assessment.

The functional components 100 also include a user input device 114 arranged to facilitate reception of input commands directly from a wearer of the hearing device 18, and a non-volatile memory 116 arranged to store programs for use by the processor 102 to implement desired functionality. The non-volatile memory 116 also stores audiogram data created as a result of carrying out hearing tests as hearing threshold data 118.

The functional components 100 also include a sound generator 120 arranged to generate sound information usable by the digital to analogue converter 112, the amplifier 111 and the speaker 110 to produce sound. In this example, the processor 102 and sound generator 120 are responsive to commands received by the hearing device 18 from a computing device such as a smartphone 14, such that a received command is interpreted by the processor 102 and the sound generator 120, and sound information produced that is usable by the digital to analogue converter 112, the amplifier 111 and the speaker 110 to create sound corresponding to the sound information. In this way, the system ensures that the sound is generated at the hearing device 18 thereby ensuring that the generated sound is a faithful representation of the desired sound, for example in terms of level and frequency. Calibration information 122 is used to ensure that the sound presented to a wearer of the hearing device 18 is at a level and frequency that accurately corresponds to the desired level and frequency.

A command sent by the computing device 14 to the hearing device 18 may use any suitable format. For example, a command may contain the following information:

[Command ID]
[Side (0=Left, 1=Right, 2=Left & Right)]
[Type (0=Continuous, 1=Pulsed)]
[Frequency (in Hz)]
[Duration (in seconds)]
[Level (dB)]

In an alternative arrangement, the sound information corresponding to the desired sounds may be generated on the computing device and streamed to the hearing device 18 for production by the speaker 110. However, with this arrangement, there is a possibility that the computing device will modify the level of the sound because the computing device, for example a smart phone, typically does not have full control over the level of sound sent to the hearing device 18.

In response to generation of a sound at the hearing device, the wearer typically responds by providing an input, such as a touch gesture, on the computing device to indicate that the sound has been heard. If a response to a sound is not received from a wearer of the hearing device 18, the system is arranged to record threshold information to indicate the minimum level of sound that the wearer is able to hear at the relevant frequency. In this way, the system creates hearing threshold data representative of hearing thresholds at a plurality of frequencies that is representative of an audiogram for the wearer.

In this example, the functional components 100 also include a noise assessment module 124 arranged to assess the level of background ambient noise and determine whether it is possible to carry out a hearing assessment based on the detected level of background noise. In this example, the noise assessment module 124 uses sound received from the microphones 106 on the hearing device 18 as in this way an accurate reading of the level of ambient sound adjacent ears of the user can be obtained.

The functional components also include an identification module 126 arranged to provide identification information on request, for example based on a request from the smartphone 14, the identification information indicative of the type of hearing device.

An example hearing assessment procedure carried out by the computing device, in this example a smartphone 14, and the hearing device 18 is illustrated in FIGS. 10 to 25 with reference to example screens displayed to a user on the smartphone 14.

Figure 10:
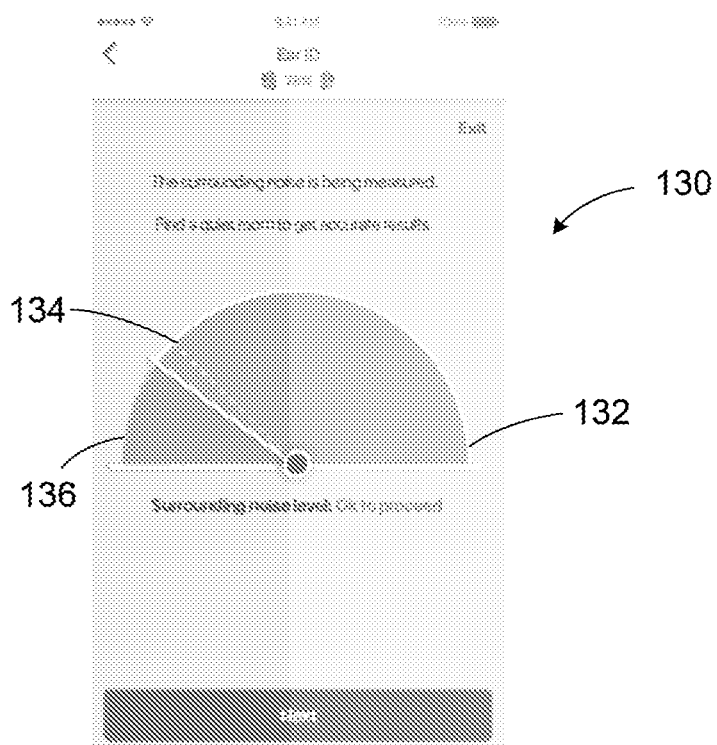
FIGS. 10 to 25 are diagrammatic representations of screens presented to a user during a hearing assessment carried out by the system.
Figure 11:
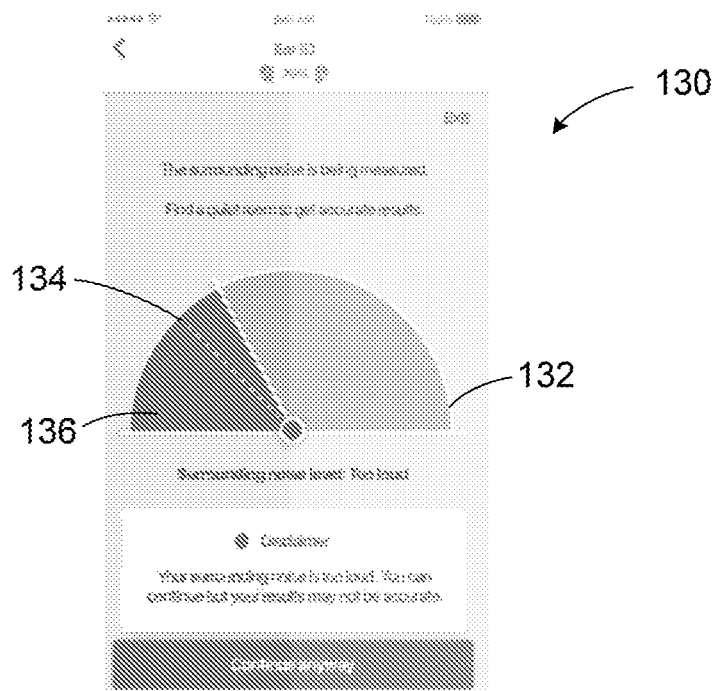

A hearing assessment is instigated by implementing the relevant software application on the smartphone 14, and after commencement of a hearing assessment procedure using the smartphone application, the smartphone 14 sends a communication to the hearing devices 18 that causes the hearing devices 18 to switch from normal mode to a fitting mode. In the fitting mode, a background noise screen 130 is displayed on the smartphone 14, as shown in FIGS. 10 and 11.

The background noise screen 130 includes a background noise indicator 132 arranged to communicate to a user whether the background noise is too high to carry out an effective hearing assessment. In this example, for this purpose, the background noise indicator 132 includes an acceptable background noise line 134 and a current noise indicator 136, in this example in the form of a sector the central angle of which is representative of the noise level. As shown in FIG. 10, a sector having a central angle that is less than an angle associated with the acceptable background noise line 134 corresponds to an acceptable background noise level. As shown in FIG. 11, a sector having a central angle that is greater than an angle associated with the acceptable background noise line 134 corresponds to an unacceptable background noise level. The acceptable and unacceptable background noise levels may be further communicated to a user by displaying the associated segments in different colours.

Figure 12:
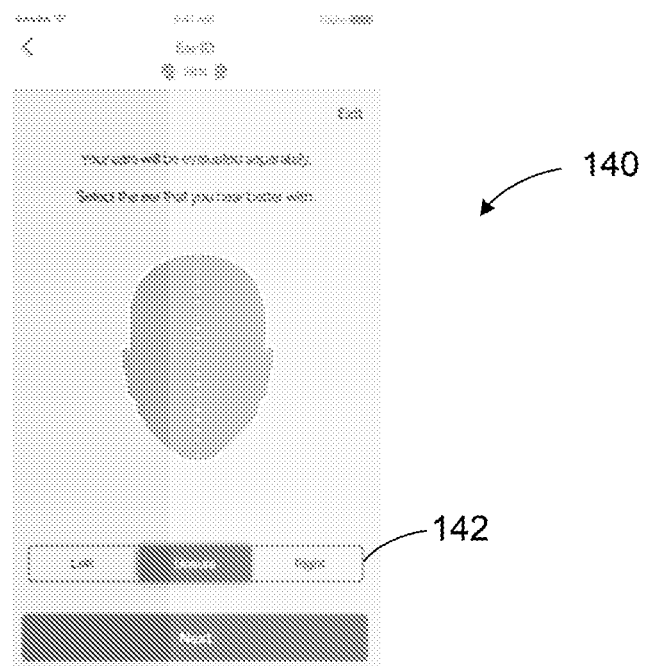
Figure 13:
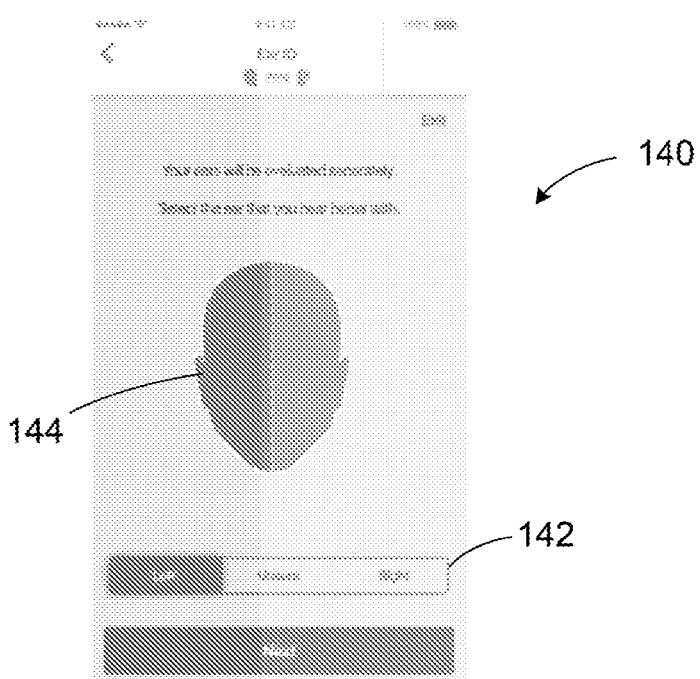

The next stage of the example hearing assessment procedure is to display an ear selection screen 140, as shown in FIGS. 12 and 13.

The ear selection screen 140 includes ear selectors 142 usable to enable a user to select that ear that is considered to provide better hearing, or to indicate that the user has no preferred ear. Selection of an ear causes a selected ear indicator 144 to highlight the selected ear, as shown in FIG. 13.

The next stage of the example hearing assessment procedure is to implement a familiarization procedure whereby a user is provided with examples of the sounds that will be presented to the user during the hearing assessment, and the user undergoes a fitting procedure whereby an assessment is made as to whether left and right hearing devices 18 are properly fitted into the user's ears. If a hearing device 18 is not properly fitted into a user's ear, leakage of low frequency sound can occur and the sound may not effectively couple to the ear to the extent that the user cannot hear the sound.

Figure 14:
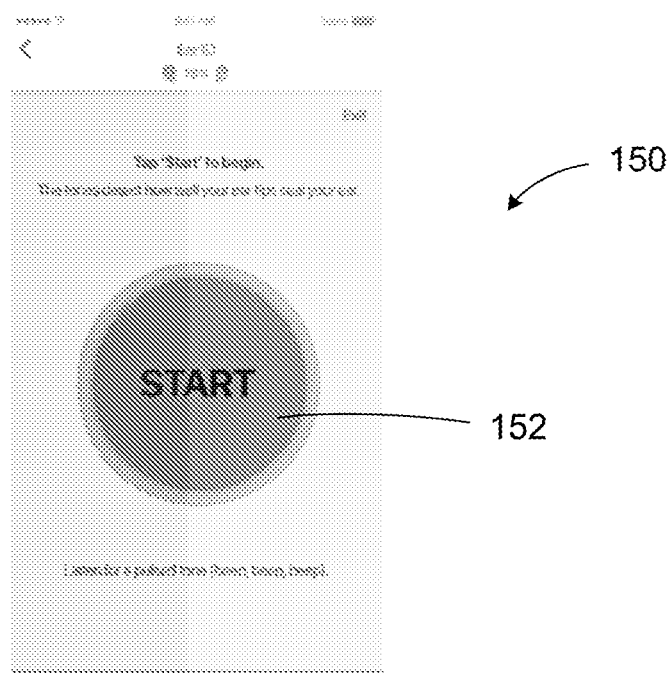
Figure 15:
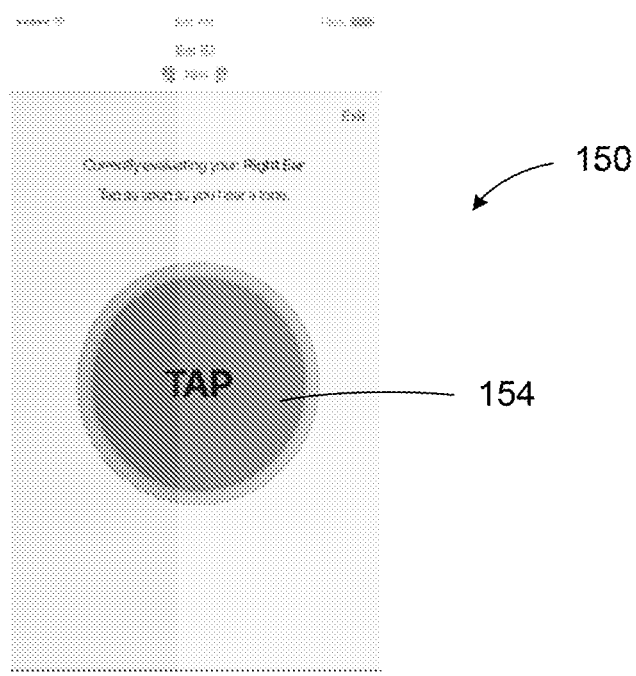

During the familiarization procedure, a familiarization screen 150, as shown in FIGS. 14 and 15, is displayed. Using the familiarization screen 150, one or more sound tones are generated at the hearing device 18 corresponding to the selected ear, or if no ear has been selected, corresponding to the right ear. The familiarization procedure is commenced by selecting a start button 152, and in response to hearing the or each sound the user presses a response button 154 to indicate that the tone has been heard.

In this example, the tone played during the familiarization procedure may be a low level low frequency tone that may be a 1 kHz tone at 60 dBHL, a 250 Hz tone at 70 dBHL, and/or a 250 Hz tone at 40 dBHL. The tone may be a continuous tone, a pulsed tone or a pulsed warble tone.

Figure 16:
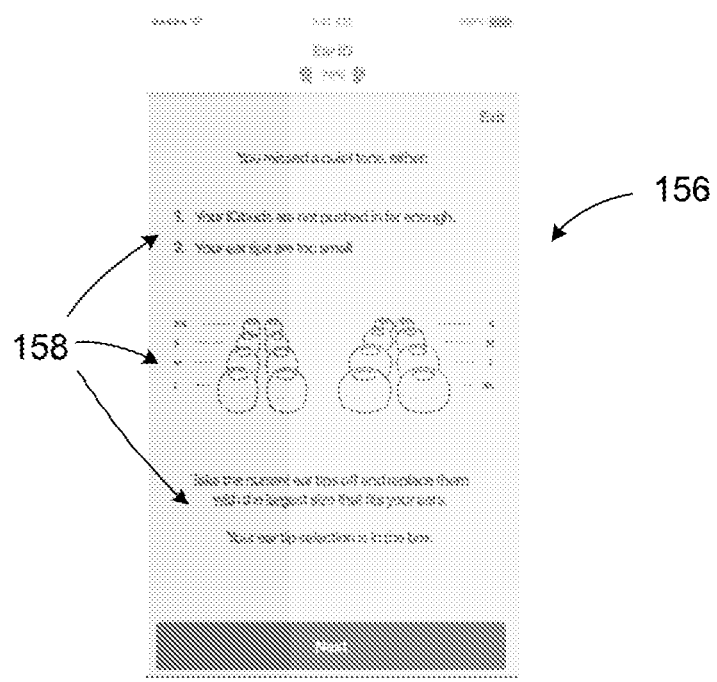

If the user does not respond to indicate that one or more of the tones have been heard, an ear tip screen 156 is displayed, as shown in FIG. 16. The ear tip screen 156 is used to advise the user that the relevant hearing device 18 may not be properly fitted in the user's ear and adjustment may be required, for example by modifying an ear tip used on the hearing device 18.

Figure 17:
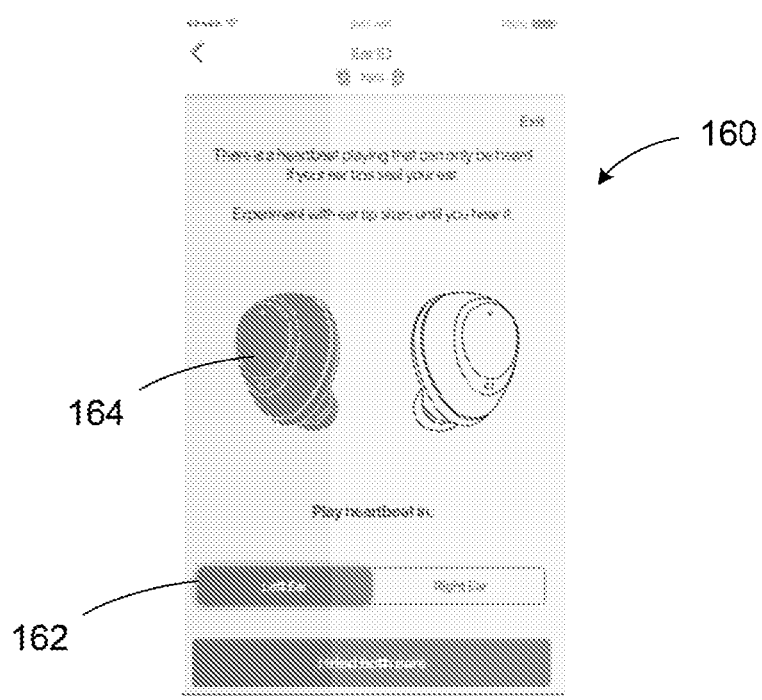

After appropriate modification of the location of the hearing device in the user's ear or replacement of the ear tip of the hearing device 18, if a response is not received to indicate that the tone has been heard, a heartbeat screen 160 is displayed, as shown in FIG. 17. At the heartbeat screen 160, the user selects the relevant ear using an ear selector 162 and the selected ear is highlighted by a selected ear indicator 164. After selection of an ear, a heartbeat tone is produced at the relevant hearing device 18 corresponding to the selected ear. The heartbeat tone is used because some people have difficulty identifying low frequency sounds, but people can usually identify a low frequency heartbeat sound.

Figure 18:
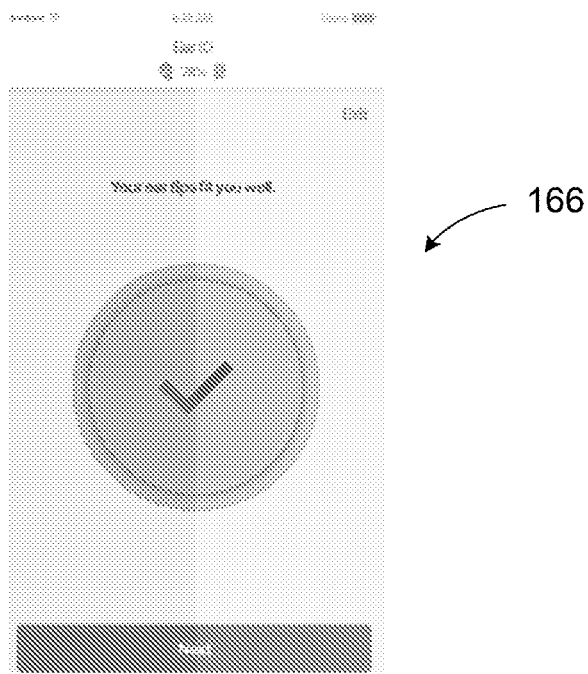

If the user has responded to indicate that either the familiarization tone or the heartbeat tone has been heard, a fitting complete screen is displayed, as shown in FIG. 18 to provide the user with confirmation that the left and right hearing devices 18 appear to be well fitted.

Figure 19:
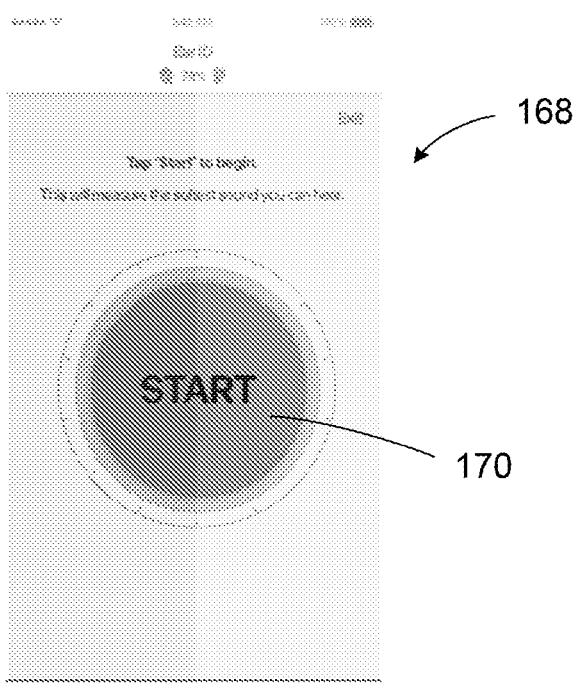

After completion of the familiarization procedure, the hearing devices switch to a hearing assessment mode and a test start screen 168, as shown in FIG. 19 is displayed on the smartphone 14. The hearing test is commenced by selecting a test start button 170 on the test start screen 168.

Figure 20:
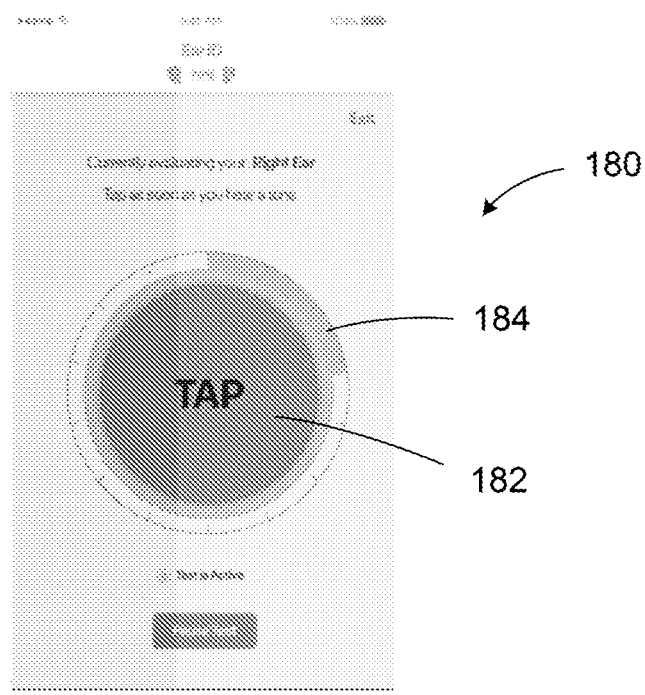
Figure 21:
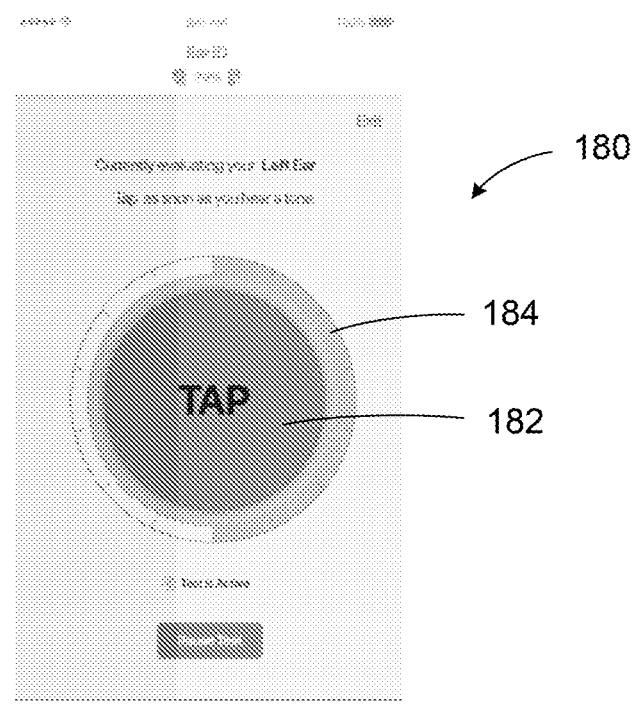

During the hearing test, a test response screen 180 is displayed as shown in FIGS. 20 and 21, and successive tones are produced for each ear in turn, for example according to the Hughson-Westlake process or Modified Hughson-Westlake process.

In this example, the tones are produced at frequency points 125 Hz, 250 Hz, 500 Hz, 1000 Hz, 1500 Hz, 2000 Hz, 3000 Hz, 4000 Hz, 6000 Hz and 8000 Hz, although it will be understood that any suitable frequency points are envisaged. For example, the number of frequency points can be reduced if a shorter test is desired, such that only frequency points 500 Hz, 1000 Hz, 2000 Hz, 3000 Hz, 4000 Hz and 6000 Hz are used. During the test, the level of each tone is increased at 5 dB increments, although it will be understood that any suitable increment is envisaged.

In this example, the tones are pulsed warble tones with a fundamental frequency corresponding to the frequency points according to the Hughson-Westlake process or Modified Hughson-Westlake process.

In response to each tone, if the tone has been heard by the user, the user presses a response button 182. Progress through the test is communicated to the user using a test progress indicator 184.

Figure 22:
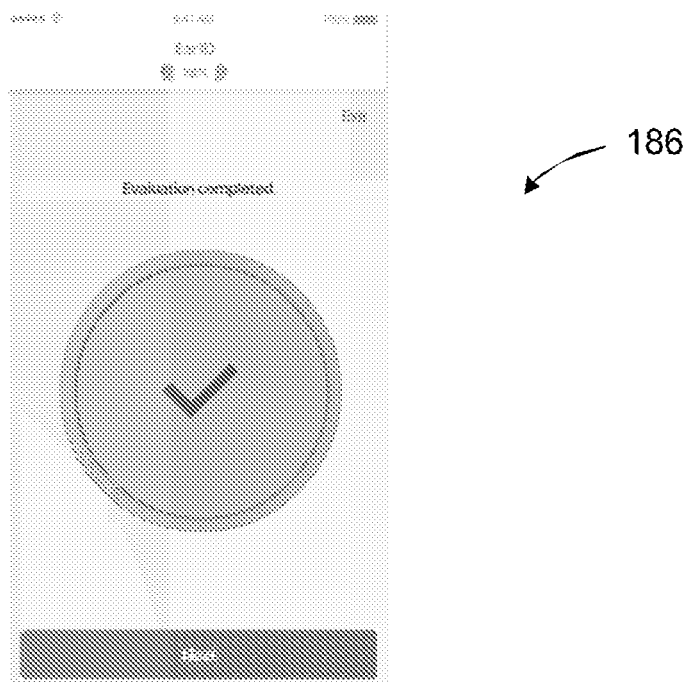

After completion of the hearing test, a test complete screen 186 is displayed, as shown in FIG. 22, to indicate to the user that the test has finished.

Figure 23:
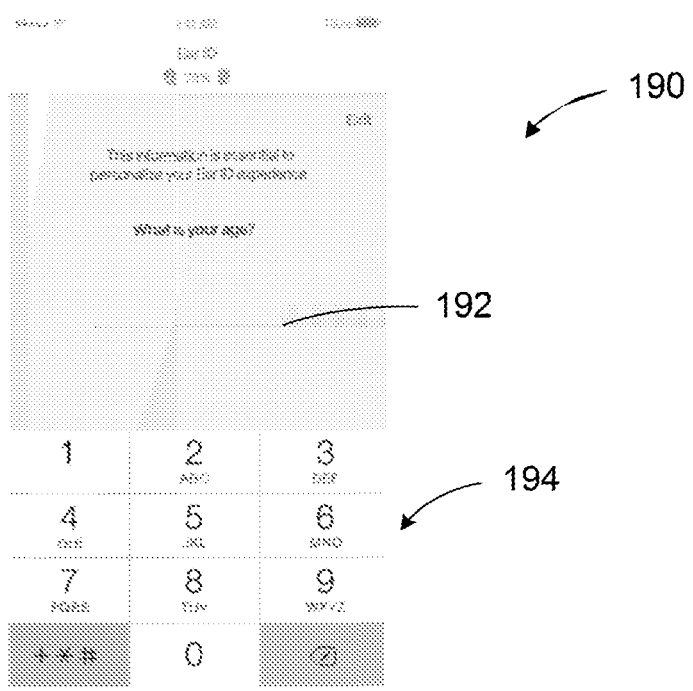
Figure 24:
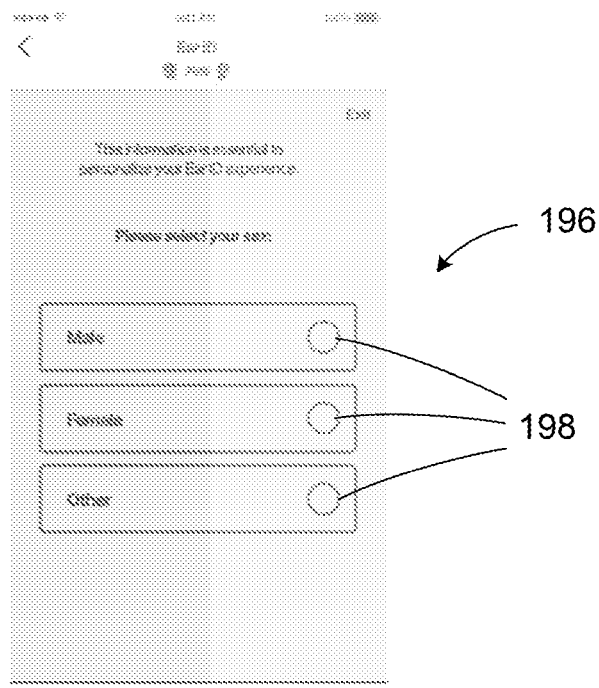

After completion of the hearing test, an age selection screen 190 as shown in FIG. 23 and a gender selection screen 196 as shown in FIG. 24 are displayed. Using the age selection screen 190, the user enters his/her age using an age field 192 and number pad 194. Using the gender selection screen 196, the user enters his/her gender using gender selections buttons 198. The age and gender of the user are required as an assessment of the hearing capabilities of the user is dependent on the age and gender of the user.

Figure 25:
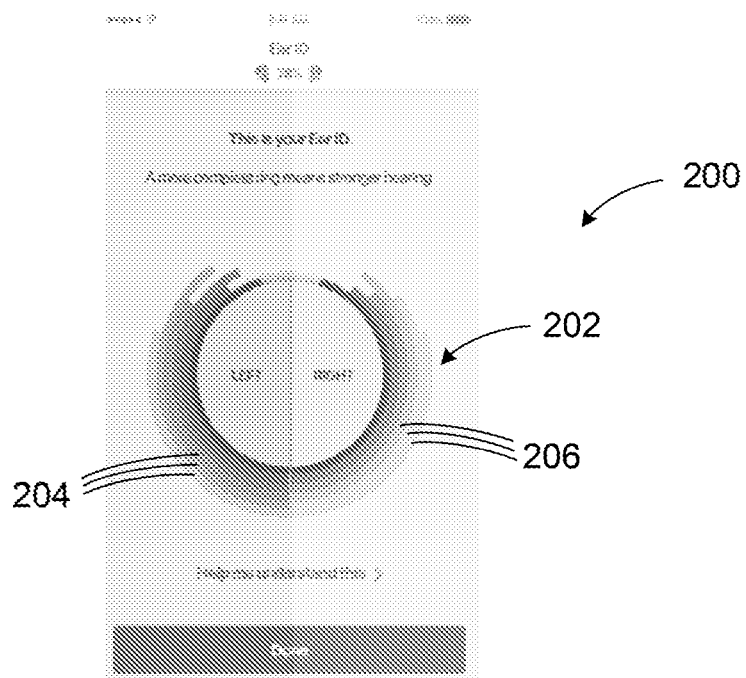

As shown in FIG. 25, a test results screen 200 is then displayed that shows the user's hearing results using a hearing results indicator 202.

In this example, the hearing results indicator 202 includes a left ear portion and a right ear portion, the right and left ear portions corresponding to hemispheres of a circle. Each ear portion includes multiple ring portions 204, 206. Each ring portion 204, 206 corresponds to a specific frequency point, for example of the Hughson-Westlake process or Modified Hughson-Westlake process, with for example the innermost ring portion corresponding to the lowest frequency point and the ring portions outwardly of the innermost ring portion progressively corresponding to successively higher frequency points. In addition, the length of each ring portion corresponds to the strength of hearing at the frequency point associated with the ring portion. The ring portions 204, 206 may be represented differently based on whether the ring portions 204, 206 are associated with the left or right ear, for example by displaying the ring portions 204, 206 in different colours, and may be represented differently based on the relevant frequency, for example by displaying the ring portions 204, 206 for each ear in different shades of the same colour.

The results indicator 202 shown in FIG. 25 indicates that the person concerned has hearing loss and, in particular, has particular difficulty hearing at the highest frequency point of the Hughson-Westlake process or Modified Hughson-Westlake process used in the hearing assessment.

It will be understood that the results indicator 202 provides a simple, efficient mechanism for communicating the hearing characteristics of a person for each separate ear in terms of strength of hearing at different frequencies to a non-professional.

In addition to the functionality described above, or alternatively, a system for configuring a hearing device may be provided that is arranged to produce recommendation information indicative of a referral to a hearing health professional or other health professional or of a recommendation to use a different hearing device 18 that has greater or more suitable capabilities, if the audiogram data indicates that a medical problem may exist, or that the hearing capabilities of the user may not be adequately improved by the hearing device 18. The recommendation information may be displayed to the user and/or electronically communicated to one or more relevant people.

For this purpose, in an embodiment, the audiogram data analysis component 42 may be arranged to consider the hearing device capabilities, for example retrieved from the hearing device database 90, with the audiogram data, and if the consideration indicates that the user requires a hearing device with greater or different capabilities than the current hearing device 18 can provide, a referral database 94 is queried by the audiogram data analysis component 42 for a hearing health professional that satisfies defined criteria, for example based on locality.

The consideration may be based on a comparison of the hearing thresholds specified in the audiogram data with the hearing device fitting range, and for example if the hearing thresholds are close to or outside an acceptable device fitting range, the audiogram data analysis component 42 is arranged to make a determination that the user should be referred.

In an embodiment, the audiogram data analysis component 42 may be arranged to produce the recommendation information if the audiogram data is within 5 dB of the audio device fitting range limits, within 10 dB of the audio device fitting range limits, or within 15 dB of the audio device fitting range limits.

The audiogram data used to compare the hearing capabilities of the user with the audio device capabilities may include air conduction hearing thresholds and bone conduction hearing threshold measurements.

In an example, the recommendation information may be produced and for example displayed to the user if the bone conduction measurements are not within 10 dB of the air conduction measurements.

The recommendation information may be produced if any frequency point in the air conduction audiogram data is 0 dB, 5 dB, 10 dB, 15 dB of the device fitting range when compared on the frequency point by frequency point basis.

The system may be arranged to implement an automated referral process wherein the location of the user is determined, for example using a GPS device or other location determining device that may be present in the computing device or through an API, and the determined location used to extract relevant hearing health professional(s) from the referral database 94. The closest hearing health professional recorded in the referral database 94 can for example be determined using conventional route finding and mapping data APIs.

In an embodiment, multiple local hearing health professionals, such as 3 local health professionals, are identified and for example displayed to the user.

The system 10 may also be arranged to compare a user's electronic calendar with an electronic calendar of the identified hearing health professional(s), for example stored in an accessible database such as the referral database 94 so that a mutually free timeslot for the user and the hearing health professional can be identified. The user's electronic calendar may be retrieved using an API on the user's smartphone.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Modifications and variations as would be apparent to a skilled addressee are determined to be within the scope of the present invention.

The invention claimed is:

1. A hearing assistance system comprising:
   a hearing assistance device configured to reproduce sounds and to assist a person to hear the sounds, the hearing assistance device including a left hearing assistance device and a right hearing assistance device; and
   a computing device in communication with the hearing assistance device;
   the computing device interacting with the hearing assistance device to implement a fitting mode wherein the hearing assistance device is caused to generate fitting sounds usable to evaluate whether the left and right hearing devices are properly fitted into respective left and right ears of the person; and
   the computing device producing a communication indicative of whether the left and right hearing assistance devices are properly fitted into respective left and right ears of the person.

2. A hearing assistance system as claimed in claim 1, wherein the fitting sounds include a low frequency tone and the computing device is arranged to determine whether each of the left and right hearing assistance devices is properly fitted into the person's ear by determining whether the user has heard the low frequency tone.

3. A hearing assistance system as claimed in claim 2, wherein the low frequency tone comprises a continuous tone, a pulsed tone, a pulsed warble tone or a heartbeat tone.

4. A hearing assistance system as claimed in claim 1, wherein the computing device is configured to restrict or prevent defined functionality of the hearing assistance device during the fitting mode.

5. A hearing assistance system as claimed in claim 4, wherein the computing device is configured to restrict or prevent the hearing assistance device from receiving telephone calls, receiving user input from controls on the hearing assistance device, or receiving streamed audio during the fitting mode.

6. A hearing assistance system as claimed in claim 1, wherein sound received at microphones of the left and right hearing assistance devices is not reproduced by speakers of the left and right hearing devices during the fitting mode.

7. A hearing assistance system as claimed in claim 1, wherein the computing device is configured to repeatedly poll the left and right hearing devices during the fitting mode, and the hearing assistance device moves from the fitting mode to a normal mode if the left and right hearing assistance devices do not receive a poll communication from the computing device after a defined period of time.

8. A hearing assistance system as claimed in claim 1, wherein the computing device is configured to implement a familiarization procedure whereby a user is provided with examples of the sounds that will be presented to the user during the fitting mode.

9. A hearing assistance system comprising:
a hearing assistance device configured to reproduce sounds and to assist a person to hear the sounds; and
a computing device in communication with the hearing assistance device;
the computing device including a processor configured to implement a hearing device configuration component that configures the hearing assistance device for the person;
the hearing device configuration component interacting with the hearing assistance device to:
implement a hearing assessment on the person using the hearing assistance device, the hearing assessment including generation of hearing assessment sounds of defined frequencies at the hearing assistance device and recording responses from the person; and
configure the hearing assistance device using the responses from the person;
wherein the system is configured to restrict or prevent defined functionality of the hearing assistance device during the hearing assessment.

10. A hearing assistance system as claimed in claim 9, wherein the computing device is configured to restrict or prevent the hearing assistance device from receiving telephone calls, receiving user input from controls on the hearing assistance device, or receiving streamed audio during the hearing assessment.

11. A system as claimed in claim 9, wherein the system is configured to assess the level of background ambient noise prior to implementation of a hearing assessment and determine whether the level of background ambient noise is sufficiently low to carry out the hearing assessment.

12. A hearing assistance system as claimed in claim 9, wherein the computing device is configured to implement a familiarization procedure whereby a user is provided with examples of the sounds that will be presented to the user during the hearing assessment.

13. A hearing assistance system comprising:
a hearing assistance device configured to reproduce sounds and to assist a person to hear the sounds; and
a computing device in communication with the hearing assistance device;
the computing device including a processor configured to implement a hearing device configuration component that configures the hearing assistance device for the person;
the hearing device configuration component interacting with the hearing assistance device to:
implement a hearing assessment on the person using the hearing assistance device, the hearing assessment including generation of hearing assessment sounds of defined frequencies at the hearing assistance device and recording responses from the person; and
configure the hearing assistance device using the responses from the person;
wherein the system is arranged to generate hearing assessment sounds consistent with the capabilities of the hearing assistance device.

14. A system as claimed in claim 13, wherein the system is arranged to query the hearing assistance device for the device capabilities.

15. A system as claimed in claim 14, wherein the system is arranged to query the hearing assistance device to obtain identification information indicative of the type of hearing assistance device, and to use the identification information to retrieve the device capabilities associated with the hearing assistance device from a storage device.

16. A system as claimed in claim 13, wherein the device capabilities include any one or more of device frequency range, maximum gain, type of ear tip fitted, and whether the hearing assistance device is an open or closed fit device.

17. A system as claimed in claim 13, wherein the system is configured to assess the level of background ambient noise prior to implementation of a hearing assessment and determine whether the level of background ambient noise is sufficiently low to carry out the hearing assessment.

18. A hearing assistance system as claimed in claim 13, wherein the computing device is configured to implement a familiarization procedure whereby a user is provided with examples of the sounds that will be presented to the user during the hearing assessment.

* * * * *